US010966717B2

(12) United States Patent
Shah et al.

(10) Patent No.: US 10,966,717 B2
(45) Date of Patent: Apr. 6, 2021

(54) SURGICAL FASTENER APPARATUS

(71) Applicant: Covidien LP, Mansfield, MA (US)

(72) Inventors: Sachin Shah, Milford, CT (US);
Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 469 days.

(21) Appl. No.: 15/377,086

(22) Filed: Dec. 13, 2016

(65) Prior Publication Data

US 2017/0196556 A1 Jul. 13, 2017

Related U.S. Application Data

(60) Provisional application No. 62/275,993, filed on Jan. 7, 2016.

(51) Int. Cl.
*A61B 17/072* (2006.01)
*A61B 17/128* (2006.01)
(Continued)

(52) U.S. Cl.
CPC ...... *A61B 17/072* (2013.01); *A61B 17/00234* (2013.01); *A61B 17/07207* (2013.01);
(Continued)

(58) Field of Classification Search
CPC ... A61B 17/072; A61B 17/30; A61B 17/1285; A61B 17/07207; A61B 17/00234;
(Continued)

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

AU 198654765 9/1986
CA 2773414 A1 11/2012
(Continued)

OTHER PUBLICATIONS

European Search Report dated May 30, 2017, issued in EP Application No. 17150572.
(Continued)

*Primary Examiner* — Robert F Long
*Assistant Examiner* — Eduardo R Ferrero
(74) *Attorney, Agent, or Firm* — Carter, DeLuca & Farrell LLP

(57) ABSTRACT

A surgical fastener apparatus includes a handle, a flexible elongate segment and an end effector having a fastener cartridge with a plurality of fasteners and an anvil, an approximator member movable relative to the longitudinal axis to cause relative movement of the fastener cartridge and the anvil between an open condition and an approximated condition, a fastener drive to deploy the fasteners from the fastener cartridge for crimping by the anvil, at least one tissue grasper at least partially extending along the end effector and movable to engage tissue and draw the tissue between the fastener cartridge and the anvil when in the open condition, and at least one manual actuator to actuate at least one of the approximator member, the fastener drive or the at least one tissue grasper.

20 Claims, 31 Drawing Sheets

(51) Int. Cl.
  *A61B 17/30* (2006.01)
  *A61B 17/00* (2006.01)
  *A61B 1/00* (2006.01)
  *A61B 90/00* (2016.01)

(52) U.S. Cl.
  CPC .......... *A61B 17/1285* (2013.01); *A61B 17/30* (2013.01); *A61B 1/00087* (2013.01); *A61B 1/00154* (2013.01); *A61B 90/37* (2016.02); *A61B 2017/00278* (2013.01); *A61B 2017/00473* (2013.01); *A61B 2017/00477* (2013.01); *A61B 2017/00827* (2013.01); *A61B 2017/07214* (2013.01); *A61B 2017/07228* (2013.01); *A61B 2017/07257* (2013.01); *A61B 2017/07271* (2013.01); *A61B 2017/306* (2013.01); *A61B 2017/308* (2013.01)

(58) Field of Classification Search
  CPC .......... A61B 90/37; A61B 2017/07257; A61B 2017/00477; A61B 2017/00473; A61B 2017/308; A61B 2017/306; A61B 2017/00278; A61B 2017/00827; A61B 2017/07214; A61B 2017/07228; A61B 2017/07271; A61B 2017/00353; A61B 1/00087; A61B 1/00154
  USPC ........................................................ 606/150
  See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,459,978 A * | 7/1984 | Kotsanis ................ A61B 90/00 600/201 |
| 4,505,414 A | 3/1985 | Filipi |
| 4,506,669 A * | 3/1985 | Blake, III ............... A61B 17/30 294/99.2 |
| 4,520,817 A | 6/1985 | Green |
| 4,589,413 A | 5/1986 | Malyshev et al. |
| 4,591,085 A * | 5/1986 | Di Giovanni ........ A61B 17/072 227/19 |
| 4,596,351 A | 6/1986 | Fedotov et al. |
| 4,602,634 A | 7/1986 | Barkley |
| 4,605,001 A | 8/1986 | Rothfuss et al. |
| 4,606,345 A * | 8/1986 | Dorband ............... A61B 17/072 112/169 |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,773,420 A * | 9/1988 | Green .................... A61B 17/11 227/178.1 |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,938,408 A * | 7/1990 | Bedi .................... A61B 17/072 227/130 |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A * | 7/1994 | Wilk .................... A61B 17/068 227/179.1 |
| 5,332,142 A | 7/1994 | Robinson et al. |
| 5,336,221 A * | 8/1994 | Anderson .............. A61B 17/12 606/27 |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A * | 2/1995 | Tsuruta ............ A61B 17/00234 606/41 |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,403,326 A * | 4/1995 | Harrison ............ A61B 17/0643 128/898 |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,737 A * | 6/1995 | Burbank ............ A61B 17/0469 606/139 |
| 5,425,745 A | 6/1995 | Green et al. |
| 5,431,322 A | 7/1995 | Green et al. |
| 5,431,323 A | 7/1995 | Smith et al. |
| 5,433,721 A * | 7/1995 | Hooven ................ A61B 17/068 227/175.1 |
| 5,441,193 A | 8/1995 | Gravener |

(56) References Cited

U.S. PATENT DOCUMENTS

| | | | |
|---|---|---|---|
| 5,445,304 | A | 8/1995 | Plyley et al. |
| 5,447,265 | A | 9/1995 | Vidal et al. |
| 5,452,837 | A | 9/1995 | Williamson, IV et al. |
| 5,454,822 | A * | 10/1995 | Schob ............... A61B 17/0469 112/169 |
| 5,456,401 | A | 10/1995 | Green et al. |
| 5,464,300 | A | 11/1995 | Crainich |
| 5,464,414 | A * | 11/1995 | Cziffer ............... A61B 17/1128 606/150 |
| 5,465,895 | A | 11/1995 | Knodel et al. |
| 5,467,911 | A | 11/1995 | Tsuruta et al. |
| 5,470,007 | A | 11/1995 | Plyley et al. |
| 5,470,010 | A | 11/1995 | Rothfuss et al. |
| 5,472,132 | A | 12/1995 | Savage et al. |
| 5,474,566 | A | 12/1995 | Alesi et al. |
| 5,476,206 | A | 12/1995 | Green et al. |
| 5,478,003 | A | 12/1995 | Green et al. |
| 5,480,089 | A | 1/1996 | Blewett |
| 5,482,197 | A | 1/1996 | Green et al. |
| 5,484,095 | A | 1/1996 | Green et al. |
| 5,484,451 | A | 1/1996 | Akopov et al. |
| 5,485,947 | A | 1/1996 | Olson et al. |
| 5,485,952 | A | 1/1996 | Fontayne |
| 5,486,185 | A | 1/1996 | Freitas et al. |
| 5,487,499 | A | 1/1996 | Sorrentino et al. |
| 5,487,500 | A | 1/1996 | Knodel et al. |
| 5,489,058 | A | 2/1996 | Plyley et al. |
| 5,490,856 | A | 2/1996 | Person et al. |
| 5,497,933 | A | 3/1996 | DeFonzo et al. |
| 5,501,689 | A | 3/1996 | Green et al. |
| 5,505,363 | A | 4/1996 | Green et al. |
| 5,507,426 | A | 4/1996 | Young et al. |
| 5,518,163 | A | 5/1996 | Hooven |
| 5,518,164 | A | 5/1996 | Hooven |
| 5,529,235 | A | 6/1996 | Boiarski et al. |
| 5,531,744 | A | 7/1996 | Nardella et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A * | 7/1996 | Bolanos ............... A61B 17/072 227/178.1 |
| 5,542,594 | A | 8/1996 | McKean et al. |
| 5,549,628 | A | 8/1996 | Cooper et al. |
| 5,551,622 | A | 9/1996 | Yoon |
| 5,553,765 | A | 9/1996 | Knodel et al. |
| 5,554,164 | A | 9/1996 | Wilson et al. |
| 5,554,169 | A | 9/1996 | Green et al. |
| 5,560,530 | A | 10/1996 | Bolanos et al. |
| 5,560,532 | A | 10/1996 | DeFonzo et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,701 | A * | 10/1996 | Huitema ............ A61B 17/07207 128/898 |
| 5,564,615 | A | 10/1996 | Bishop et al. |
| 5,571,116 | A | 11/1996 | Bolanos et al. |
| 5,573,169 | A | 11/1996 | Green et al. |
| 5,573,543 | A | 11/1996 | Akopov et al. |
| 5,575,799 | A | 11/1996 | Bolanos et al. |
| 5,575,803 | A | 11/1996 | Cooper et al. |
| 5,577,654 | A | 11/1996 | Bishop |
| 5,584,425 | A | 12/1996 | Savage et al. |
| 5,586,711 | A | 12/1996 | Plyley et al. |
| 5,588,580 | A | 12/1996 | Paul et al. |
| 5,588,581 | A | 12/1996 | Conlon et al. |
| 5,597,107 | A | 1/1997 | Knodel et al. |
| 5,601,224 | A | 2/1997 | Bishop et al. |
| 5,607,095 | A | 3/1997 | Smith et al. |
| 5,615,820 | A | 4/1997 | Viola |
| 5,618,291 | A | 4/1997 | Thompson et al. |
| 5,624,452 | A | 4/1997 | Yates |
| 5,626,587 | A | 5/1997 | Bishop et al. |
| 5,628,446 | A | 5/1997 | Geiste et al. |
| 5,630,539 | A | 5/1997 | Plyley et al. |
| 5,630,540 | A | 5/1997 | Blewett |
| 5,630,541 | A | 5/1997 | Williamson, IV et al. |
| 5,632,432 | A | 5/1997 | Schulze et al. |
| 5,634,584 | A | 6/1997 | Okorocha et al. |
| 5,636,780 | A | 6/1997 | Green et al. |
| 5,645,209 | A | 7/1997 | Green et al. |
| 5,647,526 | A | 7/1997 | Green et al. |
| 5,651,491 | A | 7/1997 | Heaton et al. |
| 5,653,373 | A | 8/1997 | Green et al. |
| 5,653,374 | A | 8/1997 | Young et al. |
| 5,653,721 | A | 8/1997 | Knodel et al. |
| 5,655,698 | A | 8/1997 | Yoon |
| 5,657,921 | A | 8/1997 | Young et al. |
| 5,658,300 | A | 8/1997 | Bito et al. |
| 5,662,258 | A | 9/1997 | Knodel et al. |
| 5,662,259 | A | 9/1997 | Yoon |
| 5,662,260 | A | 9/1997 | Yoon |
| 5,662,662 | A | 9/1997 | Bishop et al. |
| 5,662,666 | A | 9/1997 | Onuki et al. |
| 5,665,085 | A | 9/1997 | Nardella |
| 5,665,100 | A * | 9/1997 | Yoon ..................... A61B 10/06 606/139 |
| 5,667,517 | A | 9/1997 | Hooven |
| 5,669,544 | A | 9/1997 | Schulze et al. |
| 5,673,840 | A | 10/1997 | Schulze et al. |
| 5,673,841 | A | 10/1997 | Schulze et al. |
| 5,673,842 | A | 10/1997 | Bittner et al. |
| 5,674,230 | A * | 10/1997 | Tovey ................ A61B 17/0469 606/139 |
| 5,676,674 | A | 10/1997 | Bolanos et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,690,269 | A | 11/1997 | Bolanos et al. |
| 5,692,668 | A | 12/1997 | Schulze et al. |
| 5,697,542 | A | 12/1997 | Knodel et al. |
| 5,702,409 | A | 12/1997 | Rayburn et al. |
| 5,704,534 | A | 1/1998 | Huitema et al. |
| 5,706,997 | A | 1/1998 | Green et al. |
| 5,709,334 | A | 1/1998 | Sorrentino et al. |
| 5,711,472 | A | 1/1998 | Bryan |
| 5,713,505 | A | 2/1998 | Huitema |
| 5,715,988 | A | 2/1998 | Palmer |
| 5,716,366 | A | 2/1998 | Yates |
| 5,718,359 | A | 2/1998 | Palmer et al. |
| 5,725,536 | A | 3/1998 | Oberlin et al. |
| 5,725,554 | A | 3/1998 | Simon et al. |
| 5,728,110 | A | 3/1998 | Vidal et al. |
| 5,732,806 | A | 3/1998 | Foshee et al. |
| 5,735,848 | A | 4/1998 | Yates et al. |
| 5,743,456 | A | 4/1998 | Jones et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,762,256 | A | 6/1998 | Mastri et al. |
| 5,769,303 | A | 6/1998 | Knodel et al. |
| 5,769,892 | A | 6/1998 | Kingwell |
| 5,772,099 | A | 6/1998 | Gravener |
| 5,772,673 | A | 6/1998 | Cuny et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,834 | A | 7/1998 | Lucey et al. |
| 5,785,232 | A | 7/1998 | Vidal et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,810,811 | A | 9/1998 | Yates et al. |
| 5,810,855 | A | 9/1998 | Rayburn et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,109 | A | 10/1998 | McGarry et al. |
| 5,820,009 | A | 10/1998 | Melling et al. |
| 5,823,066 | A | 10/1998 | Huitema et al. |
| 5,826,776 | A | 10/1998 | Schulze et al. |
| 5,829,662 | A | 11/1998 | Allen et al. |
| 5,833,695 | A | 11/1998 | Yoon |

(56) References Cited

U.S. PATENT DOCUMENTS

| | | |
|---|---|---|
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,083,241 A * | 7/2000 | Longo ............... A61B 17/0293 227/179.1 |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,258,107 B1 * | 7/2001 | Balazs ............... A61B 17/115 227/175.1 |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Gerbi et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 * | 5/2005 | Jinno ................. B25J 3/04 600/130 |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |

(56) References Cited

U.S. PATENT DOCUMENTS

| | | | |
|---|---|---|---|
| 7,390,329 B2 * | 6/2008 | Westra | A61B 17/0401 606/139 |
| 7,396,356 B2 | 7/2008 | Mollenauer | |
| 7,398,907 B2 | 7/2008 | Racenet et al. | |
| 7,399,310 B2 | 7/2008 | Edoga et al. | |
| 7,401,720 B1 | 7/2008 | Durrani | |
| 7,401,721 B2 | 7/2008 | Holsten et al. | |
| 7,404,508 B2 | 7/2008 | Smith et al. | |
| 7,404,509 B2 | 7/2008 | Ortiz et al. | |
| 7,407,074 B2 | 8/2008 | Ortiz et al. | |
| 7,407,075 B2 | 8/2008 | Holsten et al. | |
| 7,407,077 B2 | 8/2008 | Ortiz et al. | |
| 7,407,078 B2 | 8/2008 | Shelton, IV et al. | |
| 7,416,101 B2 | 8/2008 | Shelton, IV et al. | |
| 7,419,080 B2 | 9/2008 | Smith et al. | |
| 7,419,081 B2 | 9/2008 | Ehrenfels et al. | |
| 7,419,495 B2 | 9/2008 | Menn et al. | |
| 7,422,139 B2 | 9/2008 | Shelton, IV et al. | |
| 7,424,965 B2 | 9/2008 | Racenet et al. | |
| 7,431,189 B2 | 10/2008 | Shelton, IV et al. | |
| 7,431,730 B2 | 10/2008 | Viola | |
| 7,434,715 B2 | 10/2008 | Shelton, IV et al. | |
| 7,434,717 B2 | 10/2008 | Shelton, IV et al. | |
| 7,438,208 B2 | 10/2008 | Larson | |
| 7,438,209 B1 | 10/2008 | Hess et al. | |
| 7,441,684 B2 | 10/2008 | Shelton, IV et al. | |
| 7,441,685 B1 | 10/2008 | Boudreaux | |
| 7,448,525 B2 | 11/2008 | Shelton, IV et al. | |
| 7,451,904 B2 | 11/2008 | Shelton, IV | |
| 7,455,208 B2 | 11/2008 | Wales et al. | |
| 7,455,676 B2 | 11/2008 | Holsten et al. | |
| 7,458,494 B2 | 12/2008 | Matsutani et al. | |
| 7,461,767 B2 | 12/2008 | Viola et al. | |
| 7,462,185 B1 | 12/2008 | Knodel | |
| 7,464,846 B2 | 12/2008 | Shelton, IV et al. | |
| 7,464,847 B2 | 12/2008 | Viola et al. | |
| 7,464,848 B2 | 12/2008 | Green et al. | |
| 7,464,849 B2 | 12/2008 | Shelton, IV et al. | |
| 7,467,740 B2 | 12/2008 | Shelton, IV et al. | |
| 7,472,814 B2 | 1/2009 | Mastri et al. | |
| 7,472,815 B2 | 1/2009 | Shelton, IV et al. | |
| 7,472,816 B2 | 1/2009 | Holsten et al. | |
| 7,473,258 B2 | 1/2009 | Clauson et al. | |
| 7,481,347 B2 | 1/2009 | Roy | |
| 7,481,348 B2 | 1/2009 | Marczyk | |
| 7,481,349 B2 | 1/2009 | Holsten et al. | |
| 7,481,824 B2 | 1/2009 | Boudreaux et al. | |
| 7,487,899 B2 | 2/2009 | Shelton, IV et al. | |
| 7,490,749 B2 | 2/2009 | Schall et al. | |
| 7,494,039 B2 | 2/2009 | Racenet et al. | |
| 7,500,979 B2 | 3/2009 | Hueil et al. | |
| 7,503,474 B2 | 3/2009 | Hillstead et al. | |
| 7,506,790 B2 | 3/2009 | Shelton, IV | |
| 7,506,791 B2 | 3/2009 | Omaits et al. | |
| 7,510,107 B2 | 3/2009 | Timm et al. | |
| 7,513,408 B2 | 4/2009 | Shelton, IV et al. | |
| 7,517,356 B2 | 4/2009 | Heinrich | |
| 7,537,602 B2 | 5/2009 | Whitman | |
| 7,543,729 B2 | 6/2009 | Ivanko | |
| 7,543,730 B1 | 6/2009 | Marczyk | |
| 7,543,731 B2 | 6/2009 | Green et al. | |
| 7,552,854 B2 | 6/2009 | Wixey et al. | |
| 7,556,185 B2 | 7/2009 | Viola | |
| 7,556,186 B2 | 7/2009 | Milliman | |
| 7,559,450 B2 | 7/2009 | Wales et al. | |
| 7,559,452 B2 | 7/2009 | Wales et al. | |
| 7,559,453 B2 | 7/2009 | Heinrich et al. | |
| 7,559,937 B2 | 7/2009 | de la Torre et al. | |
| 7,565,993 B2 | 7/2009 | Milliman et al. | |
| 7,568,603 B2 | 8/2009 | Shelton, IV et al. | |
| 7,568,604 B2 | 8/2009 | Ehrenfels et al. | |
| 7,571,845 B2 | 8/2009 | Viola | |
| 7,575,144 B2 | 8/2009 | Ortiz et al. | |
| 7,584,880 B2 | 9/2009 | Racenet et al. | |
| 7,588,174 B2 | 9/2009 | Holsten et al. | |
| 7,588,175 B2 | 9/2009 | Timm et al. | |
| 7,588,176 B2 | 9/2009 | Timm et al. | |
| 7,588,177 B2 | 9/2009 | Racenet | |
| 7,597,229 B2 | 10/2009 | Boudreaux et al. | |
| 7,597,230 B2 | 10/2009 | Racenet et al. | |
| 7,600,663 B2 | 10/2009 | Green | |
| 7,604,150 B2 | 10/2009 | Boudreaux | |
| 7,604,151 B2 | 10/2009 | Hess et al. | |
| 7,607,557 B2 | 10/2009 | Shelton, IV et al. | |
| 7,611,038 B2 | 11/2009 | Racenet et al. | |
| 7,617,961 B2 | 11/2009 | Viola | |
| 7,624,902 B2 | 12/2009 | Marczyk et al. | |
| 7,624,903 B2 | 12/2009 | Green et al. | |
| 7,631,793 B2 | 12/2009 | Rethy et al. | |
| 7,631,794 B2 | 12/2009 | Rethy et al. | |
| 7,635,073 B2 | 12/2009 | Heinrich | |
| 7,635,074 B2 | 12/2009 | Olson et al. | |
| 7,635,373 B2 | 12/2009 | Ortiz | |
| 7,637,409 B2 | 12/2009 | Marczyk | |
| 7,637,410 B2 | 12/2009 | Marczyk | |
| 7,641,091 B2 | 1/2010 | Olson et al. | |
| 7,641,095 B2 | 1/2010 | Viola | |
| 7,644,848 B2 | 1/2010 | Swayze et al. | |
| 7,648,055 B2 | 1/2010 | Marczyk | |
| 7,651,017 B2 | 1/2010 | Ortiz et al. | |
| 7,654,431 B2 | 2/2010 | Hueil et al. | |
| 7,658,311 B2 | 2/2010 | Boudreaux | |
| 7,658,312 B2 | 2/2010 | Vidal et al. | |
| 7,665,646 B2 | 2/2010 | Prommersberger | |
| 7,665,647 B2 | 2/2010 | Shelton, IV et al. | |
| 7,669,746 B2 | 3/2010 | Shelton, IV | |
| 7,670,334 B2 | 3/2010 | Hueil et al. | |
| 7,673,780 B2 | 3/2010 | Shelton, IV et al. | |
| 7,673,781 B2 | 3/2010 | Swayze et al. | |
| 7,673,782 B2 | 3/2010 | Hess et al. | |
| 7,673,783 B2 | 3/2010 | Morgan et al. | |
| 7,678,121 B1 | 3/2010 | Knodel | |
| 7,681,772 B2 | 3/2010 | Green et al. | |
| 7,682,367 B2 | 3/2010 | Shah et al. | |
| 7,682,368 B1 | 3/2010 | Bombard et al. | |
| 7,690,547 B2 | 4/2010 | Racenet et al. | |
| 7,694,865 B2 | 4/2010 | Scirica | |
| 7,699,205 B2 | 4/2010 | Ivanko | |
| 7,703,653 B2 | 4/2010 | Shah et al. | |
| 7,721,931 B2 | 5/2010 | Shelton, IV et al. | |
| 7,721,933 B2 | 5/2010 | Ehrenfels et al. | |
| 7,721,935 B2 | 5/2010 | Racenet et al. | |
| 7,726,537 B2 | 6/2010 | Olson et al. | |
| 7,726,538 B2 | 6/2010 | Holsten et al. | |
| 7,726,539 B2 | 6/2010 | Holsten et al. | |
| 7,731,072 B2 | 6/2010 | Timm et al. | |
| 7,735,703 B2 | 6/2010 | Morgan et al. | |
| 7,740,159 B2 | 6/2010 | Shelton, IV et al. | |
| 7,740,160 B2 | 6/2010 | Viola | |
| 7,743,960 B2 * | 6/2010 | Whitman | A61B 17/07207 227/180.1 |
| 7,744,628 B2 | 6/2010 | Viola | |
| 7,753,245 B2 | 7/2010 | Boudreaux et al. | |
| 7,753,248 B2 | 7/2010 | Viola | |
| 7,757,924 B2 | 7/2010 | Gerbi et al. | |
| 7,757,925 B2 | 7/2010 | Viola et al. | |
| 7,762,445 B2 | 7/2010 | Heinrich et al. | |
| 7,766,209 B2 | 8/2010 | Baxter, III et al. | |
| 7,766,210 B2 | 8/2010 | Shelton, IV et al. | |
| 7,766,924 B1 | 8/2010 | Bombard et al. | |
| 7,766,928 B2 | 8/2010 | Ezzat et al. | |
| 7,770,774 B2 | 8/2010 | Mastri et al. | |
| 7,770,775 B2 | 8/2010 | Shelton, IV et al. | |
| 7,776,057 B2 * | 8/2010 | Laufer | A61B 17/0401 606/139 |
| 7,776,060 B2 | 8/2010 | Mooradian et al. | |
| 7,780,055 B2 | 8/2010 | Scirica et al. | |
| 7,784,662 B2 | 8/2010 | Wales et al. | |
| 7,789,283 B2 | 9/2010 | Shah | |
| 7,789,889 B2 | 9/2010 | Zubik et al. | |
| 7,793,812 B2 | 9/2010 | Moore et al. | |
| 7,793,814 B2 | 9/2010 | Racenet et al. | |
| 7,794,475 B2 | 9/2010 | Hess et al. | |
| 7,798,385 B2 | 9/2010 | Boyden et al. | |

(56) References Cited

U.S. PATENT DOCUMENTS

| | | |
|---|---|---|
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 * | 9/2011 | Marczyk ............ A61B 17/07207 227/175.1 |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |

(56) References Cited

U.S. PATENT DOCUMENTS

| | | |
|---|---|---|
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |

(56) References Cited

U.S. PATENT DOCUMENTS

| | | |
|---|---|---|
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniftin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |

(56) References Cited

U.S. PATENT DOCUMENTS

| | | |
|---|---|---|
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,937,626 B2 * | 4/2018 | Rockrohr ............. B25J 15/0226 |
| 10,159,425 B2 * | 12/2018 | Marczyk ................ A61B 5/065 |
| 2002/0042620 A1 * | 4/2002 | Julian ............... A61B 17/00234 |
| | | 606/130 |
| 2003/0015203 A1 * | 1/2003 | Makower ......... A61B 17/12022 |
| | | 128/831 |
| 2003/0120285 A1 | 6/2003 | Kortenbach |
| 2003/0167055 A1 * | 9/2003 | Kolata ................... A61B 17/08 |
| | | 606/1 |
| 2003/0216754 A1 * | 11/2003 | Kraemer ............ A61B 17/0644 |
| | | 606/142 |
| 2004/0082963 A1 * | 4/2004 | Gannoe ................ A61B 17/072 |
| | | 606/153 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0023325 A1 * | 2/2005 | Gresham ............. A61B 17/115 |
| | | 227/176.1 |
| 2005/0119524 A1 | 6/2005 | Sekine et al. |
| 2005/0149072 A1 * | 7/2005 | DeVries .................. A61B 1/32 |
| | | 606/153 |
| 2005/0216055 A1 | 9/2005 | Scirica et al. |

(56) References Cited

U.S. PATENT DOCUMENTS

| | | |
|---|---|---|
| 2006/0020271 A1* | 1/2006 | Stewart ............. A61B 17/0057 606/139 |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0038232 A1* | 2/2007 | Kraemer ............ A61B 17/0401 606/153 |
| 2007/0073341 A1 | 3/2007 | Smith et al. |
| 2007/0084897 A1 | 4/2007 | Shelton et al. |
| 2007/0088373 A1* | 4/2007 | Baker ................. A61B 17/068 606/153 |
| 2007/0102472 A1 | 5/2007 | Shelton |
| 2007/0106317 A1 | 5/2007 | Shelton et al. |
| 2007/0112359 A1* | 5/2007 | Kimura ................ A61B 17/122 606/142 |
| 2007/0114261 A1* | 5/2007 | Ortiz ................... A61B 17/064 227/175.1 |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2007/0246508 A1* | 10/2007 | Green ............. A61B 17/07207 227/180.1 |
| 2007/0282356 A1* | 12/2007 | Sonnenschein ...... A61B 17/068 606/153 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0294179 A1* | 11/2008 | Balbierz ............ A61B 17/0643 606/151 |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2008/0308607 A1* | 12/2008 | Timm ............. A61B 17/07207 227/176.1 |
| 2008/0314958 A1* | 12/2008 | Scirica ............. A61B 17/07207 227/175.2 |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0125040 A1* | 5/2009 | Hambly ................. A61B 17/30 606/148 |
| 2009/0242610 A1 | 10/2009 | Shelton, IV et al. |
| 2009/0250501 A1* | 10/2009 | Sonnenschein .... A61B 17/0057 227/176.1 |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0036197 A1* | 2/2010 | Mesallum ........... A61B 17/3423 600/104 |
| 2010/0038403 A1* | 2/2010 | D'Arcangelo ........ A61B 17/072 227/180.1 |
| 2010/0048988 A1* | 2/2010 | Pastorelli ............ A61B 1/00087 600/104 |
| 2010/0069942 A1 | 3/2010 | Shelton, IV |
| 2010/0106185 A1* | 4/2010 | Kassab ............ A61B 17/00491 606/213 |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0082456 A1* | 4/2011 | Welt ..................... A61B 17/295 606/45 |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1* | 8/2011 | Whitman ......... A61B 17/07207 227/178.1 |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0024934 A1* | 2/2012 | Shelton, IV ........ A61B 17/1114 227/180.1 |
| 2012/0024935 A1* | 2/2012 | Shelton, IV ........ A61B 17/1114 227/180.1 |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0060264 A1* | 3/2013 | Schurr ............... A61B 17/0643 606/151 |
| 2013/0068815 A1 | 3/2013 | Bruewer et al. |
| 2013/0068816 A1 | 3/2013 | Mandakolathur Vasudevan et al. |
| 2013/0068818 A1* | 3/2013 | Kasvikis .......... A61B 17/07207 227/175.2 |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |

(56) References Cited

U.S. PATENT DOCUMENTS

| | | |
|---|---|---|
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153626 A1 | 6/2013 | Felder et al. |
| 2013/0153636 A1 | 6/2013 | Shelton, IV et al. |
| 2013/0153641 A1 | 6/2013 | Shelton, IV et al. |
| 2013/0153642 A1* | 6/2013 | Felder ............... A61B 17/07207 227/181.1 |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0231697 A1* | 9/2013 | Viola ................. A61B 17/0643 606/201 |
| 2013/0256380 A1 | 10/2013 | Schmid et al. |
| 2013/0277410 A1 | 10/2013 | Fernandez et al. |
| 2013/0334280 A1* | 12/2013 | Krehel .............. A61B 17/07207 227/176.1 |
| 2014/0005479 A1* | 1/2014 | Loske ................ A61B 1/00073 600/115 |
| 2014/0005663 A1* | 1/2014 | Heard ................ A61B 18/1445 606/41 |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0058418 A1 | 2/2014 | Romley |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0222051 A1 | 8/2014 | Miyamoto et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0263573 A1* | 9/2014 | Jankowski ........... A61B 17/072 227/180.1 |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0032119 A1* | 1/2015 | Kuroda ................ A61B 17/221 606/113 |
| 2015/0048143 A1 | 2/2015 | Scheib et al. |
| 2015/0053737 A1* | 2/2015 | Leimbach ........ A61B 17/07207 227/175.1 |
| 2015/0053740 A1* | 2/2015 | Shelton, IV ..... A61B 17/07207 227/175.2 |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0223809 A1* | 8/2015 | Scheib ............. A61B 17/07292 227/180.1 |
| 2015/0250474 A1 | 9/2015 | Abbott et al. |
| 2015/0297225 A1 | 10/2015 | Huitema et al. |
| 2015/0313676 A1* | 11/2015 | Deodhar .............. A61B 17/295 606/130 |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058439 A1* | 3/2016 | Shelton, IV ......... A61B 17/068 227/176.1 |
| 2016/0058440 A1* | 3/2016 | Dinardo ........... A61B 17/07207 227/177.1 |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |

(56) References Cited

U.S. PATENT DOCUMENTS

| | | |
|---|---|---|
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0086822 A1* | 3/2017 | Scheib ............... A61B 17/1155 |
| 2018/0199941 A1* | 7/2018 | Thompson ....... A61B 17/07207 |

FOREIGN PATENT DOCUMENTS

| | | | |
|---|---|---|---|
| CA | 2884962 A1 | 11/2015 | |
| DE | 2744824 A1 | 4/1978 | |
| DE | 3114135 A1 | 10/1982 | |
| DE | 4213426 A1 | 10/1992 | |
| DE | 4300307 A1 | 7/1994 | |
| EP | 0041022 A1 | 12/1981 | |
| EP | 0136950 A2 | 4/1985 | |
| EP | 0140552 A2 | 5/1985 | |
| EP | 0156774 A2 | 10/1985 | |
| EP | 0213817 A1 | 3/1987 | |
| EP | 0216532 A1 | 4/1987 | |
| EP | 0220029 A1 | 4/1987 | |
| EP | 0273468 A2 | 7/1988 | |
| EP | 0324166 A2 | 7/1989 | |
| EP | 0324635 A1 | 7/1989 | |
| EP | 0324637 A1 | 7/1989 | |
| EP | 0324638 A1 | 7/1989 | |
| EP | 0365153 A1 | 4/1990 | |
| EP | 0369324 A1 | 5/1990 | |
| EP | 0373762 A1 | 6/1990 | |
| EP | 0380025 A2 | 8/1990 | |
| EP | 0399701 A1 | 11/1990 | |
| EP | 0449394 A2 | 10/1991 | |
| EP | 0484677 A1 | 5/1992 | |
| EP | 0489436 A1 | 6/1992 | |
| EP | 0503662 A1 | 9/1992 | |
| EP | 0514139 A2 | 11/1992 | |
| EP | 0536903 A2 | 4/1993 | |
| EP | 0537572 A2 | 4/1993 | |
| EP | 0539762 A1 | 5/1993 | |
| EP | 0545029 A1 | 6/1993 | |
| EP | 0552050 A2 | 7/1993 | |
| EP | 0552423 A2 | 7/1993 | |
| EP | 0579038 A1 | 1/1994 | |
| EP | 0589306 A2 | 3/1994 | |
| EP | 0591946 A1 | 4/1994 | |
| EP | 0592243 A2 | 4/1994 | |
| EP | 0593920 A1 | 4/1994 | |
| EP | 0598202 A1 | 5/1994 | |
| EP | 0598579 A1 | 5/1994 | |
| EP | 0600182 A2 | 6/1994 | |
| EP | 0621006 A1 | 10/1994 | |
| EP | 0621009 A1 | 10/1994 | |
| EP | 0656188 A2 | 6/1995 | |
| EP | 0666057 A2 | 8/1995 | |
| EP | 0705571 A1 | 4/1996 | |
| EP | 0 760 230 A1 | 3/1997 | |
| EP | 1531739 A2 | 5/2005 | |
| EP | 1952769 A2 | 8/2008 | |
| EP | 2090253 A2 | 8/2009 | |
| EP | 2090254 A1 | 8/2009 | |
| EP | 2583630 A2 | 4/2013 | |
| EP | 2586382 A2 | 5/2013 | |
| EP | 2907456 A1 | 8/2015 | |
| FR | 391239 A | 10/1908 | |
| FR | 2542188 A1 | 9/1984 | |
| FR | 2660851 A1 | 10/1991 | |
| FR | 2681775 A1 | 4/1993 | |
| GB | 1352554 A | 5/1974 | |
| GB | 1452185 A | 10/1976 | |
| GB | 1555455 A | 11/1979 | |
| GB | 2048685 A | 12/1980 | |
| GB | 2070499 A | 9/1981 | |
| GB | 2141066 A | 12/1984 | |
| GB | 2165559 A | 4/1986 | |
| JE | 2903159 A1 | 7/1980 | |
| JP | 51-149985 | 12/1976 | |
| JP | 2001-87272 | 4/2001 | |
| JP | 2005537093 A | 12/2005 | |
| JP | 2015173729 A | 10/2015 | |
| SU | 659146 A1 | 4/1979 | |
| SU | 728848 A1 | 4/1980 | |
| SU | 980703 A1 | 12/1982 | |
| SU | 990220 A1 | 1/1983 | |
| WO | 08302247 | 7/1983 | |
| WO | 89/10094 A1 | 11/1989 | |
| WO | 9210976 A1 | 7/1992 | |
| WO | 9308754 A1 | 5/1993 | |
| WO | 9314706 A1 | 8/1993 | |
| WO | 2004/032760 A2 | 4/2004 | |
| WO | 2007078988 A2 | 7/2007 | |
| WO | 2008141288 A1 | 11/2008 | |
| WO | 2009071070 A2 | 6/2009 | |
| WO | 2013073523 A1 | 5/2013 | |
| WO | 2014080862 A1 | 5/2014 | |
| WO | 20150191887 A1 | 12/2015 | |

OTHER PUBLICATIONS

European Office Action dated Oct. 25, 2019, issued in EP Appln. No. 17150572.

Chinese Office Action dated Jul. 27, 2020, issued in Chinese Appln. No. 201710011092, 10 pages.

Japanese Office Action dated Oct. 16, 2020, issued in corresponding Japanese Appln. No. 2017000344, 7 pages.

* cited by examiner

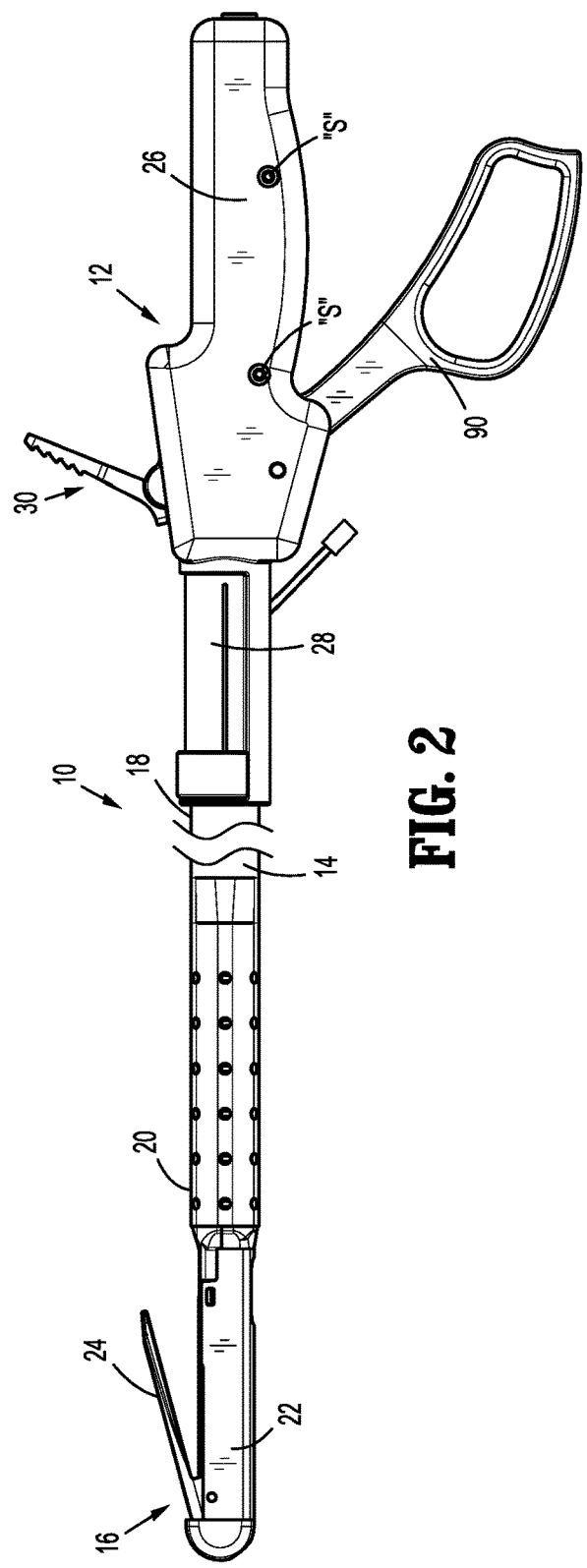
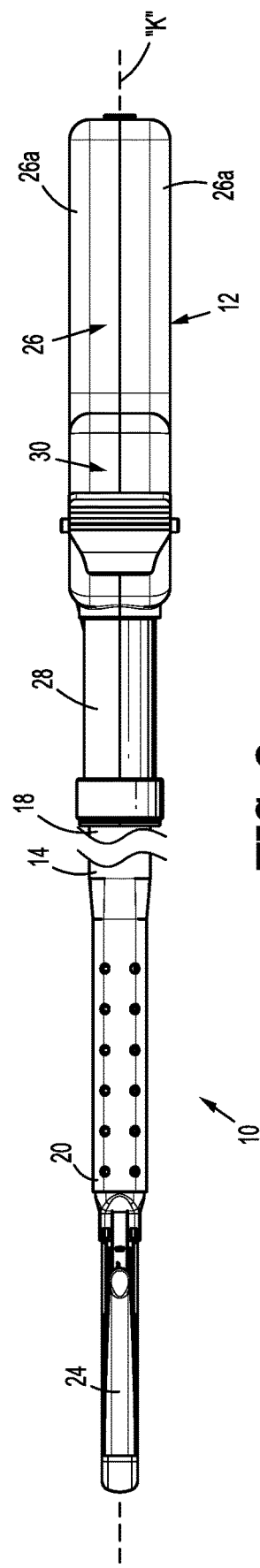
FIG. 2
FIG. 3

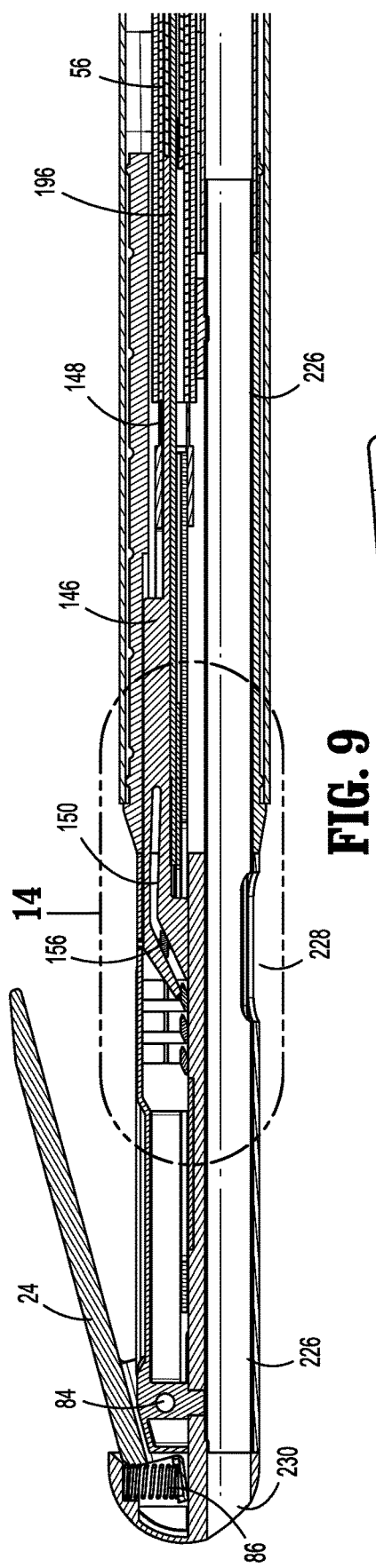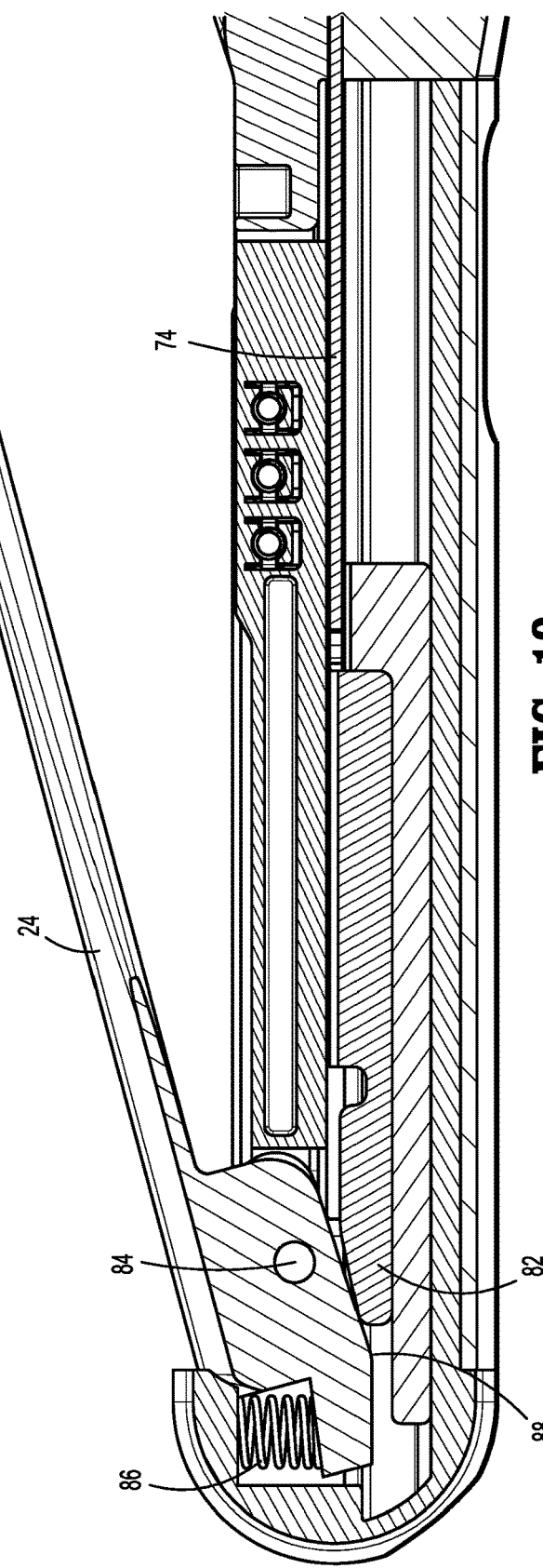

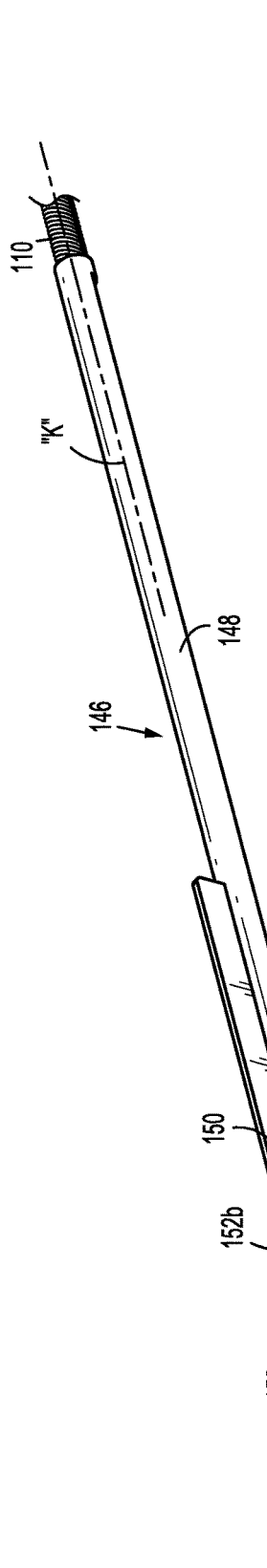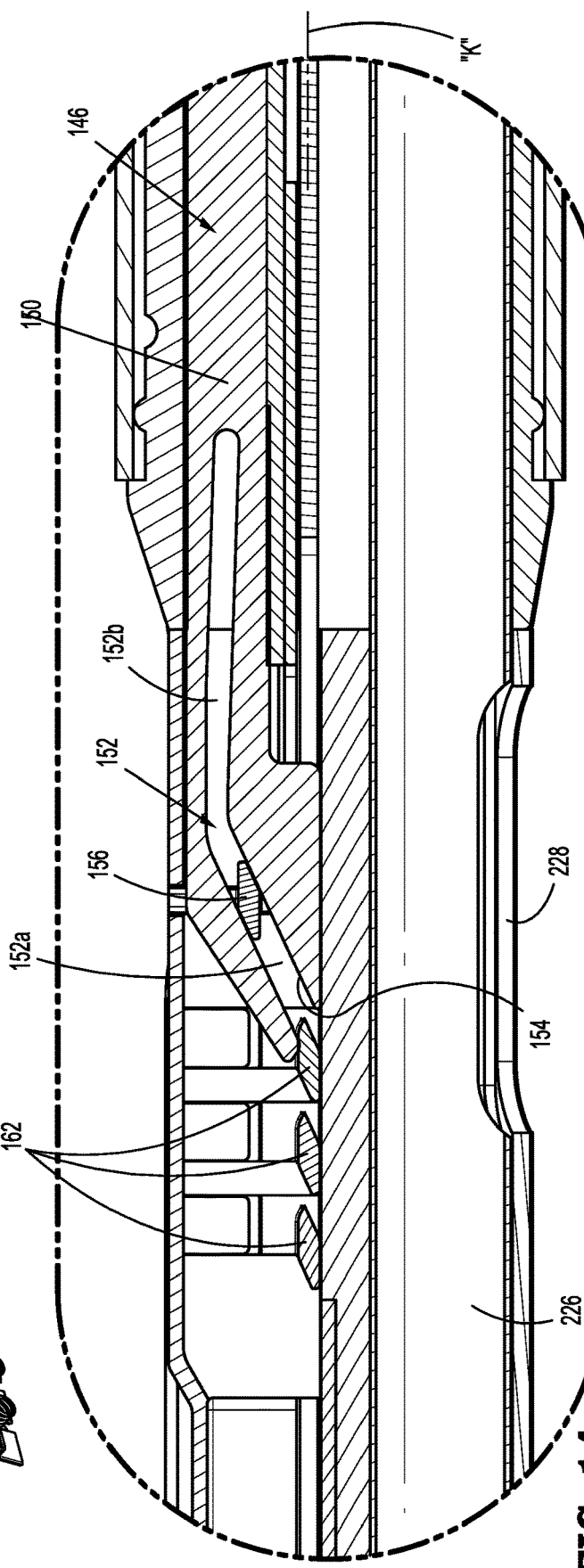
FIG. 13
FIG. 14

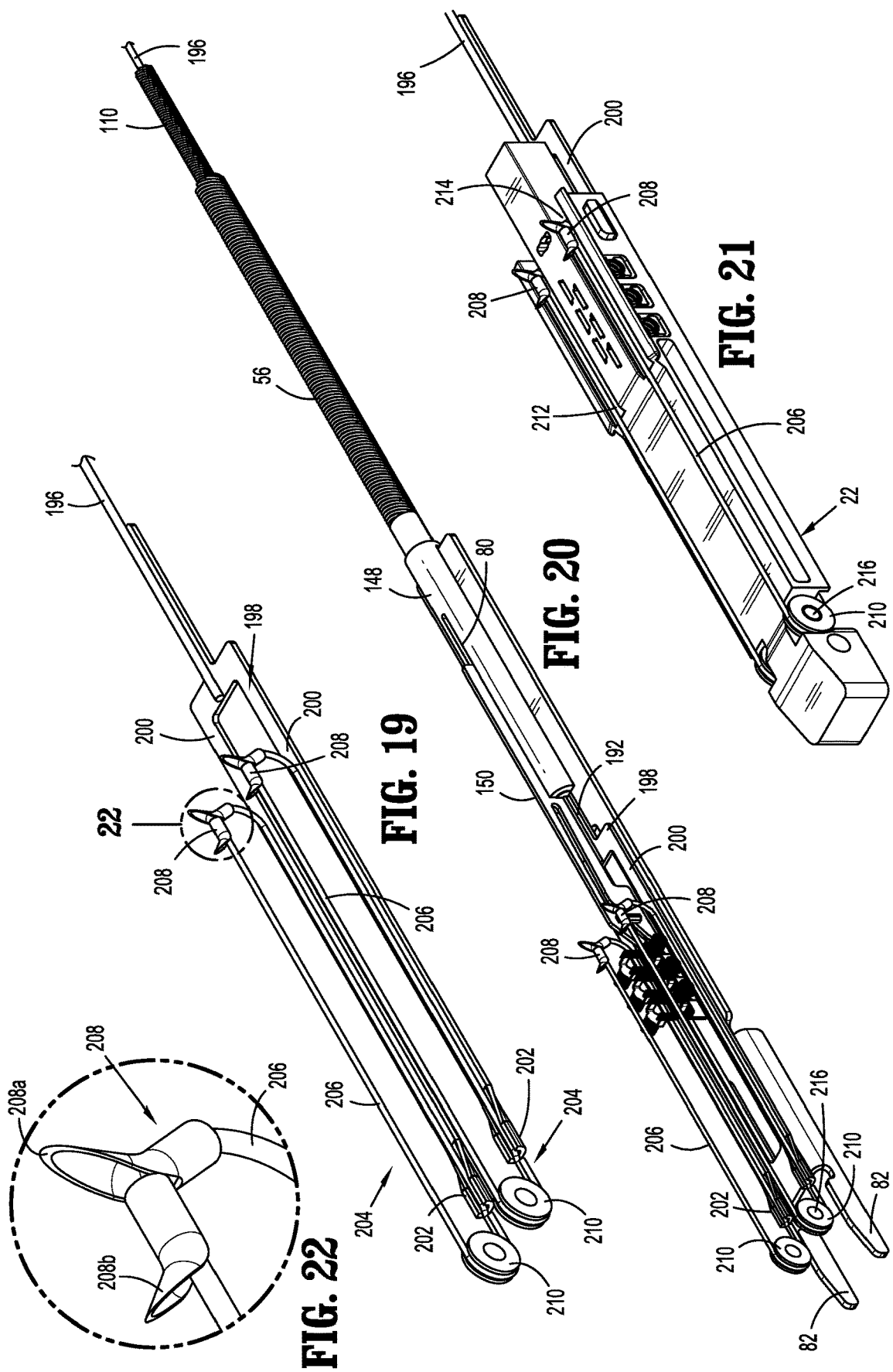

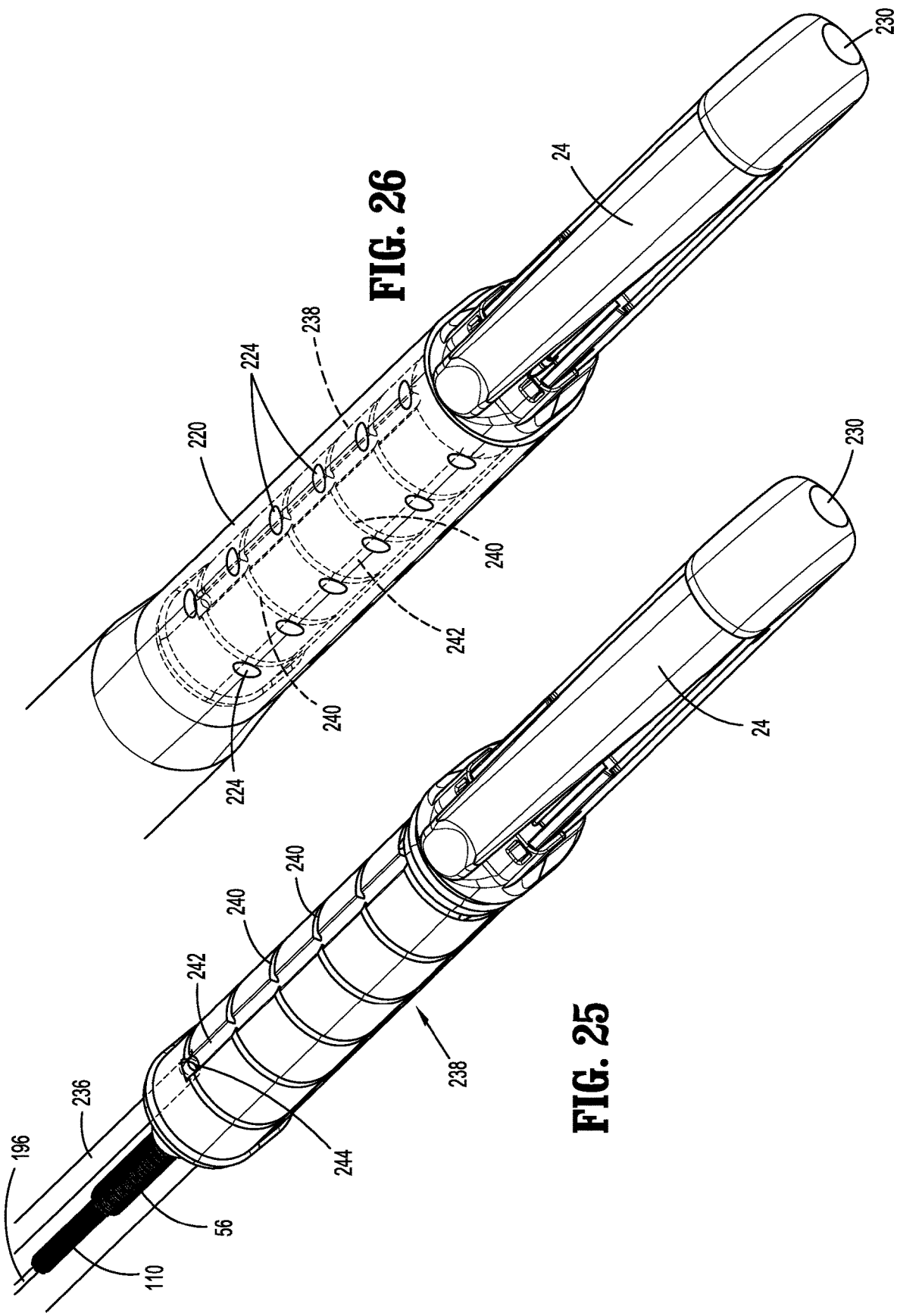

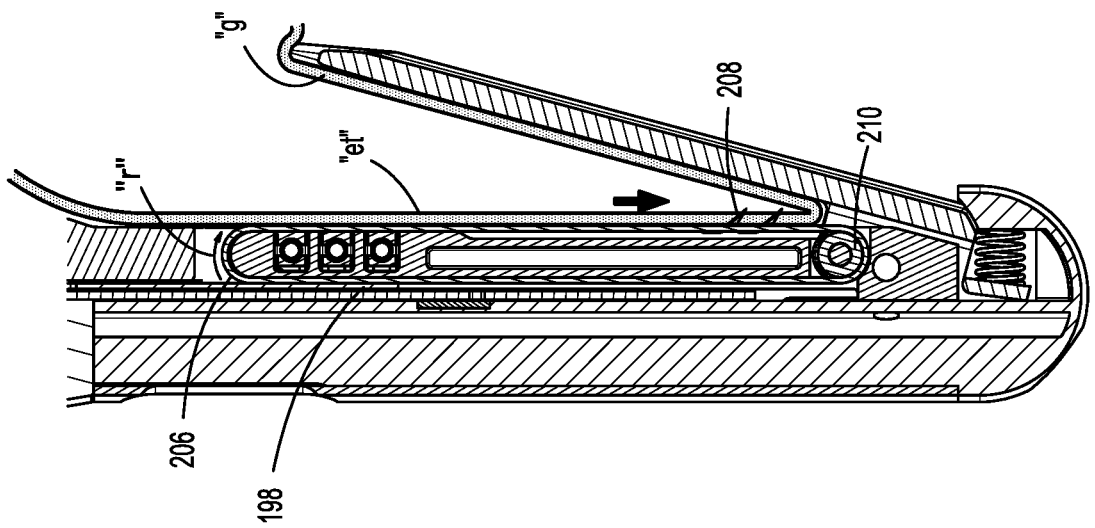
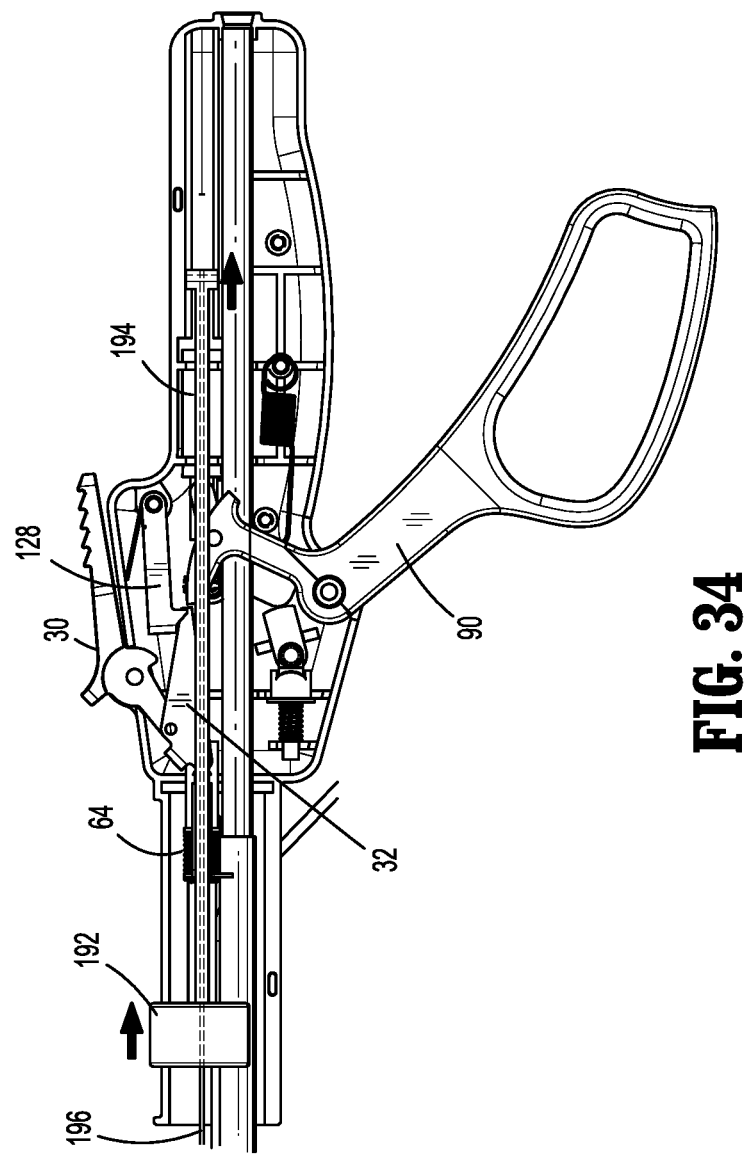
FIG. 35
FIG. 34

SURGICAL FASTENER APPARATUS

CROSS-REFERENCE TO RELATED APPLICATIONS

This application claims the benefit of and priority to U.S. Provisional Patent Application No. 62/275,993 filed Jan. 7, 2016, the entire disclosure of which is incorporated by reference herein.

BACKGROUND

1. Technical Field

The present disclosure relates to a surgical fastener apparatus, and, in particular, relates to a surgical fastener apparatus for performing an incisionless fundoplication (TIF) procedure for treatment of gastroesophageal reflux disease.

2. Description of Related Art

Gastroesophageal reflux disease (GERD) is a common gastroesophageal disorder in which stomach contents leak into the lower esophagus due to a dysfunction of the lower esophageal sphincter. As a result, patients suffer numerous symptoms including heartburn, pulmonary disorders, and chest pain. Chronic GERD subjects the esophagus to ulcer formation, esophagitis, and numerous other complications. Advances in drug therapy for GERD include histamine receptor blockers (PEPCID™, ZANTAC', etc.) which reduce stomach acid secretion and OMEPRAZOLE™ which may completely shut off stomach acid (achlorhydria). Although drugs may provide short term relief, drugs do not address the underlying problem of lower esophageal sphincter dysfunction.

Invasive and minimally invasive fundoplication procedures for the treatment of GERD involve gathering, wrapping and suturing the fundus of the stomach around the lower end of the esophagus and the lower esophageal sphincter to reconstruct the anti-reflux valve. Although these procedures have been relatively successful in preventing acid reflux and reducing symptoms associated therewith, drawbacks include concerns of abdominal surgery and intra-operative risk of perforation of the esophagus and/or of the cardia. More recent transoral incisionless fundoplication (TIF) procedures involve introducing an instrument into the esophageal tract through the mouth and reconstructing the lower esophageal sphincter or anti-reflux valve entirely within the stomach with the instrument. The TIF procedures have proven to be highly effective in treating acid reflux and provide the benefits of eliminating abdominal incisions, preventing scarring and reducing recovery time.

SUMMARY

Accordingly, the present disclosure is directed to further improvements in apparatuses and associated methods for performing transoral incisionless fundoplication (TIF). In one aspect, a surgical fastener apparatus includes a handle, a flexible elongate segment extending from the handle, an end effector mounted to the elongate segment and having a fastener cartridge with a plurality of fasteners and an anvil, an approximator member coupled to the end effector and movable relative to the longitudinal axis to cause relative movement of the fastener cartridge and the anvil between an open condition and an approximated condition, a fastener drive operatively coupled to the fastener cartridge and movable to deploy the fasteners from the fastener cartridge for forming by the anvil, at least one tissue grasper at least partially extending along the end effector and movable relative to the longitudinal axis and configured to engage and draw tissue portions between the fastener cartridge and the anvil when in the open condition, and at least one manual actuator mounted relative to the handle to actuate at least one of the approximator member, the fastener drive or the at least one tissue grasper.

In embodiments, the at least one tissue grasper is mounted for movement to the fastener cartridge. In certain embodiments, first and second tissue graspers are provided. The first and second tissue graspers are radially or laterally spaced relative to the longitudinal axis. In some embodiments, a grasper actuator is mounted relative to the handle and operatively coupled to the first and second tissue graspers. The grasper actuator is movable to cause corresponding longitudinal movement of the first and second tissue graspers to draw the tissue portions between the fastener cartridge and the anvil.

In certain aspects, the fastener apparatus includes a grasper drive operatively coupled to the grasper actuator and movable upon movement of the grasper actuator, and first and second pulley mechanisms coupled to respective first and second tissue graspers and to the grasper drive, and being actuable upon corresponding movement of the grasper actuator and the grasper drive. In embodiments, the first and second pulley mechanisms each include a closed loop to which the respective first and second tissue graspers are secured. The closed loops are movable to distally advance the first and second tissue graspers to draw the tissue portions between the fastener cartridge and the anvil.

In some embodiments, a manually operable firing trigger is mounted relative to the handle and coupled to the fastener drive. The firing trigger is movable to cause corresponding movement of the fastener drive to deploy the fasteners from the fastener cartridge. In embodiments, an approximator actuator is mounted relative to the handle and operatively coupled to the approximator member. The approximator actuator is movable relative to the handle between a first position and a second position to cause corresponding movement of the fastener cartridge and the anvil between the open condition and the approximated condition. In certain embodiments, a trigger lock is couplable to the firing trigger. The trigger lock is configured to prevent actuation of the firing trigger when the fastener cartridge and the anvil are in the open condition and permit actuation of the firing trigger when the fastener cartridge and the anvil are in the approximated condition. In some embodiments, the trigger lock includes a lock member, which is movable between a lock position and a release position relative to the firing trigger. In certain aspects, the approximator actuator is operatively couplable to the lock member whereby, upon movement of the approximator actuator to the second position, the lock member is moved to the release position. In some embodiments, the lock member is normally biased to the lock position and the approximator actuator is normally biased to the first position.

In certain embodiments, the fastener apparatus includes a vacuum conduit extending along the elongate segment and having at least one fluid port adjacent the distal end of the elongate segment. The vacuum conduit is couplable to a vacuum source to subject tissue surrounding the elongate segment to negative pressure. In embodiments, the elongate segment includes a vacuum distributor mounted adjacent the distal end of the elongate segment, and has a plurality of vacuum grooves in fluid communication with the at least one fluid port for conveying the negative pressure. In some embodiments, the elongate segment includes an outer sleeve coaxially mounted about the vacuum distributor and has a plurality of vacuum apertures in fluid communication with the vacuum grooves of the vacuum distributor for conveying the negative pressure.

In embodiments, a manually operable safety button is mounted to the handle and operably couplable with the firing trigger. The safety button is movable between a secured position relative to the firing trigger to prevent movement of the firing trigger and an unsecured position to release the firing trigger. In aspects, a safety biasing member is mounted to the handle and engageable with the safety button with the safety biasing member selectively retaining the safety button in the secured position.

In other embodiments, the handle and the elongate segment define an endoscope channel therethrough for reception of an endoscope. In embodiments, the elongate segment defines a lateral visualization window in visual communication with the endoscope channel to permit lateral viewing with the endoscope.

The fastener apparatus of the present disclosure may be utilized to create or reconstruct a reflux valve through a transoral approach, without removal of the apparatus during the fundoplication procedure and under complete visualization. The valve created or reconstructed by the fastener apparatus possesses sufficient length and circumference to substantially return the normal functioning of the reflux valve. The various mechanisms incorporated within the fastener apparatus enhance usability and effectiveness, and also eliminate potential of inadvertent activation until the components are properly positioned relative to the tissue and the clinician is prepared to initiate the procedure.

Other advantages of the present disclosure will be appreciated from the following description.

BRIEF DESCRIPTION OF THE DRAWINGS

Embodiments of the present disclosure will be appreciated by reference to the accompanying drawings wherein:

FIG. 2 is a side elevation view of the surgical fastener apparatus of FIG. 1 illustrating the end effector in the open condition;

FIG. 3 is a top plan view of the surgical fastener apparatus of FIG. 1;

FIG. 9 is a side cross-sectional view of the distal end of the elongate segment of the surgical fastener apparatus;

FIG. 10 is an enlarged side cross-sectional view illustrating the anvil of the end effector in the open condition and the cam drive in a retracted position;

FIG. 13 is a perspective view of some of the components of the fastener firing mechanism within the flexible elongate segment;

FIG. 14 is an enlarged view of the area of detail identified in FIG. 9 illustrating the firing cam and pushers of the fastener firing mechanism;

FIG. 19 is a perspective view illustrating components of the tissue grasping mechanism within the elongate segment and within the end effector;

FIG. 20 is a perspective view illustrating components of the approximator mechanism, the fastener firing mechanism and the tissue grasping mechanism within the elongate segment and within the end effector;

FIG. 21 is a perspective view illustrating components of the tissue grasping mechanism within the end effector;

FIG. 22 is an enlarged view of the area of detail depicted in FIG. 19 illustrating the tissue grasper of the tissue grasping mechanism;

FIG. 25 is a perspective view of the distal end of the elongate segment with the outer sleeve removed illustrating the vacuum distributor of the vacuum mechanism;

FIG. 26 is a perspective view of the distal end of the elongate segment illustrating the vacuum apertures within the outer sleeve;

FIG. 34 is a side elevation view of the handle with portions of the handle frame removed illustrating movement of the grasper actuator to cause corresponding movement of the tissue grasper to draw gastric and esophageal tissue within the end effector;

FIG. 35 is a side cross-sectional view illustrating the gastric and esophageal tissue drawn within the end effector;

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

Figure 1:
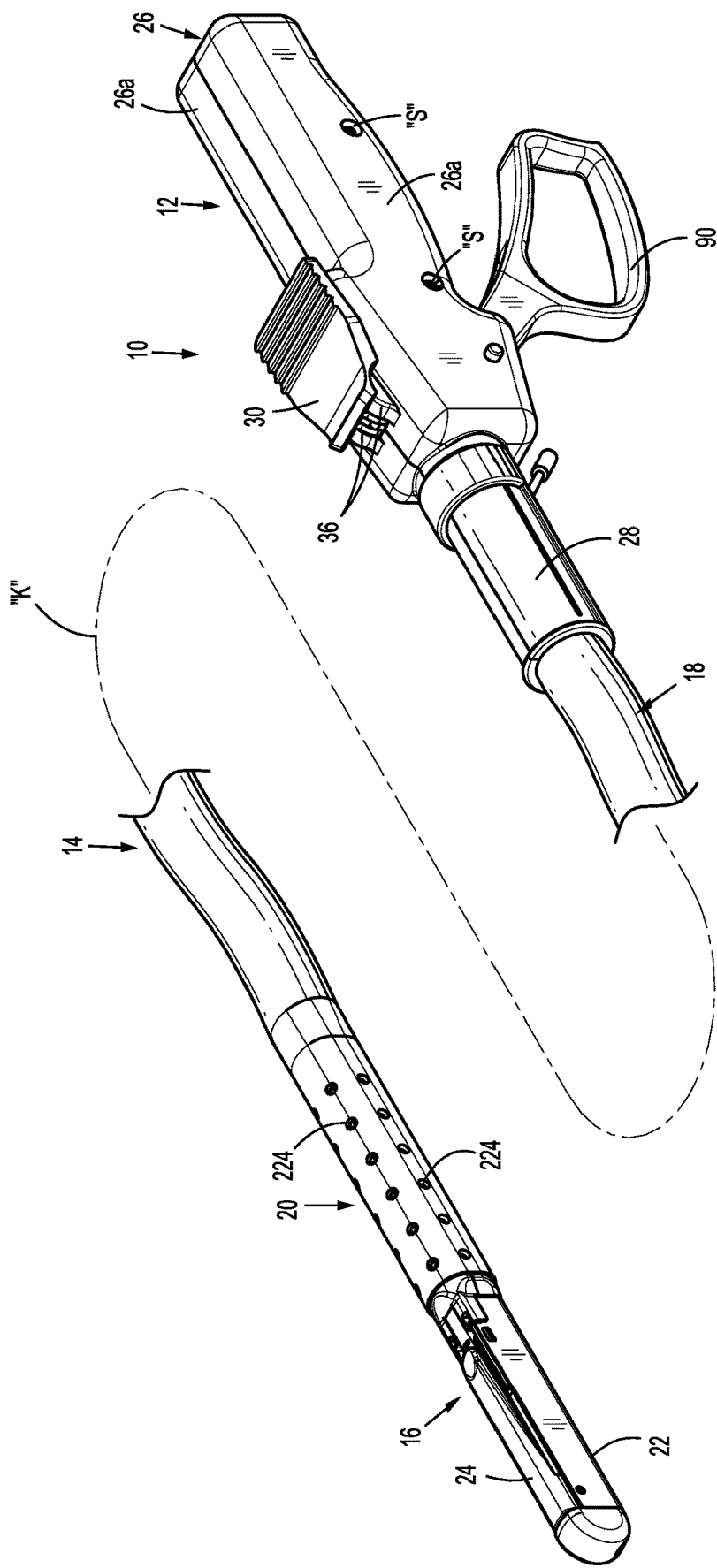
FIG. 1 is a perspective view of the surgical fastener apparatus in accordance with the principles of the present disclosure illustrating the handle, the flexible elongate segment depending from the handle and the end effector.

Referring now to the drawings where like reference numerals indicate similar components throughout the several views, FIGS. 1-3 illustrate the surgical fastener apparatus 10 of the present disclosure. The surgical fastener apparatus 10 may be adapted to apply a plurality of fasteners or staples to tissue in connection with the fastening of tissue together in a number of surgical procedures and has particular application, e.g., in a transoral incisionless fundoplication (TIF) procedure in reconstructing or recreating the anti-reflux valve. The fastener apparatus 10 includes a handle 12, a flexible elongate segment 14 connected to the handle 12, and an end effector 16 mounted to the elongate segment 14 remote from the handle 12. The elongate segment 14 defines a longitudinal axis "k" and has proximal and distal ends 18, 20. The end effector 16 is adapted to perform a fastening or stapling function and incorporates a fastener cartridge 22 and an anvil 24.

In general, the fastener apparatus 10 includes an approximator mechanism which selectively moves the end effector 16 between an approximated condition (FIG. 1) and an open condition (FIGS. 2-3), a tissue grasping mechanism which draws tissue, e.g., gastric and esophageal tissue within, or relative to, the end effector 16 when in the open condition thereof, a fastener firing mechanism which sequentially deploys fasteners from the end effector 16 to secure the tissue, and a vacuum mechanism for securing the elongate segment 14 relative to tissue, e.g., the esophageal tract. The fastener apparatus 10 may further include a trigger lockout associated with the firing mechanism for locking the firing mechanism when the end effector 16 is in the open condition and a manually operable safety, controllable by the clinician, for preventing activation of the firing mechanism until the clinician is prepared to initiate the fastening procedure. These mechanisms will each be discussed in detail hereinbelow.

With continued reference to FIGS. 1-3, the handle 12 may be any handle assembly having at least one actuator, and in some embodiments, two or more actuators adapted to control operation of the end effector 16. In one embodiment, the handle 12 includes a plurality of manually operable actuators for controlling operation of the fastener apparatus 10. Alternatively or additionally, the handle 12 may be powered incorporating a motor and supporting circuitry to operate the end effector 16. The handle 12 may include a handle frame 26 consisting of frame half sections 26a coupled to each other via conventional means including screws "s" and/or adhesives. The handle frame 26 defines a forward or distal cylindrical handle segment 28. The handle frame 26 encloses the operating components of the handle 12, and may be contoured to facilitate engagement by the clinician.

Figure 4:
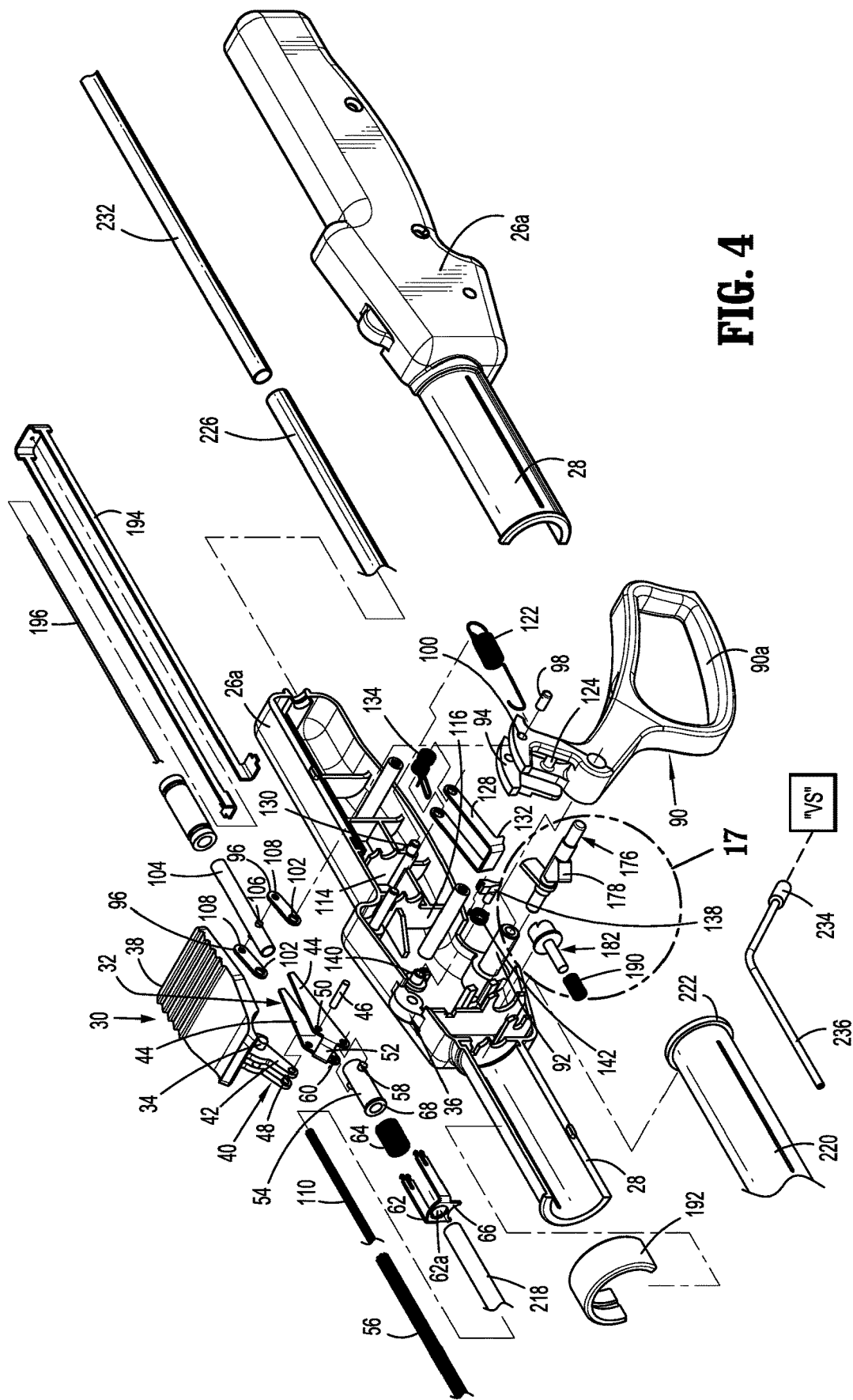
FIG. 4 is an exploded perspective view of the handle of the surgical fastener apparatus of FIG. 1.
Figure 5:
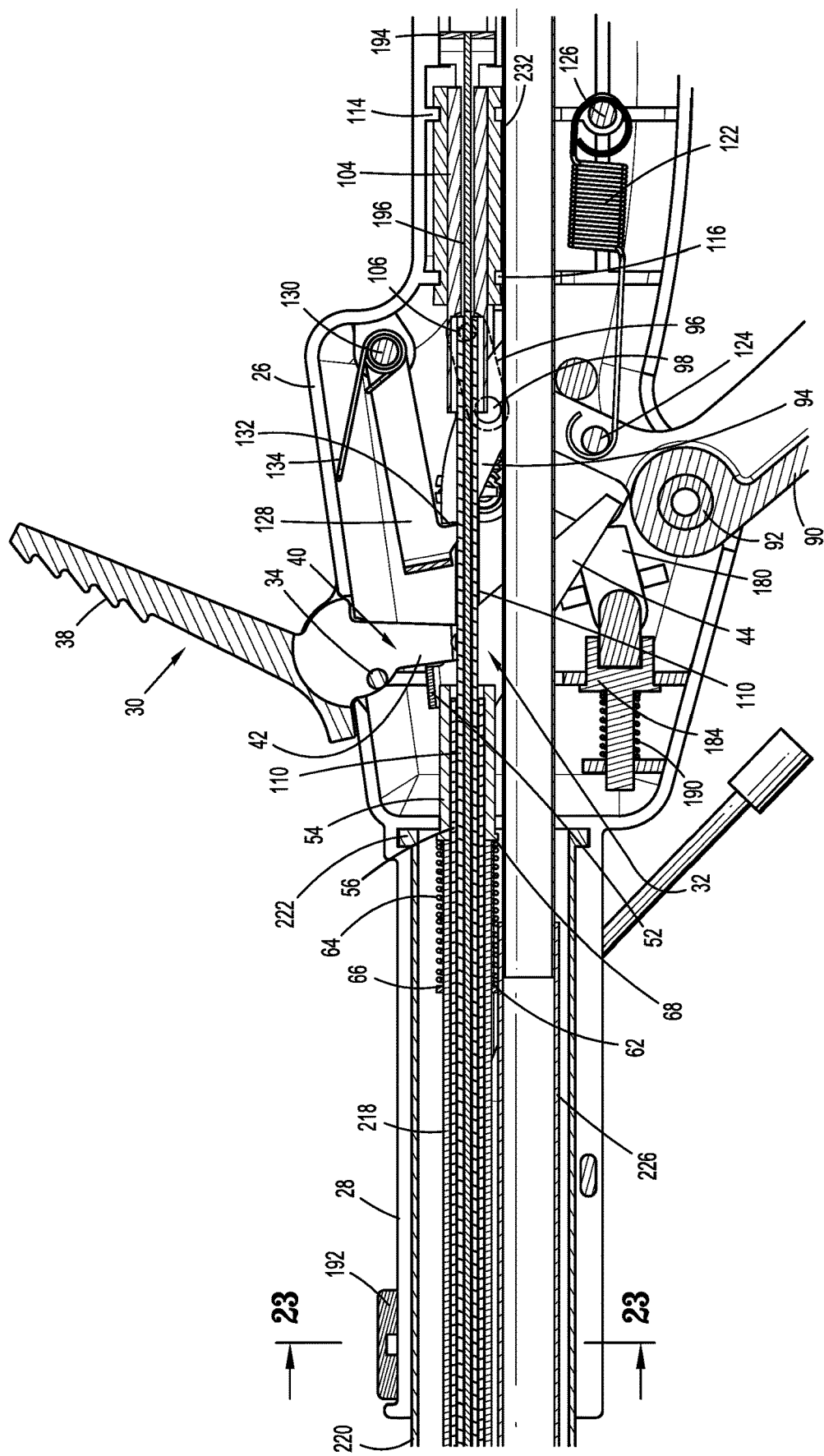
FIG. 5 is a side cross-sectional view of the handle of the surgical fastener apparatus prior to activation of the approximator mechanism, the tissue grasping mechanism and the fastener firing mechanism.
Figure 6:
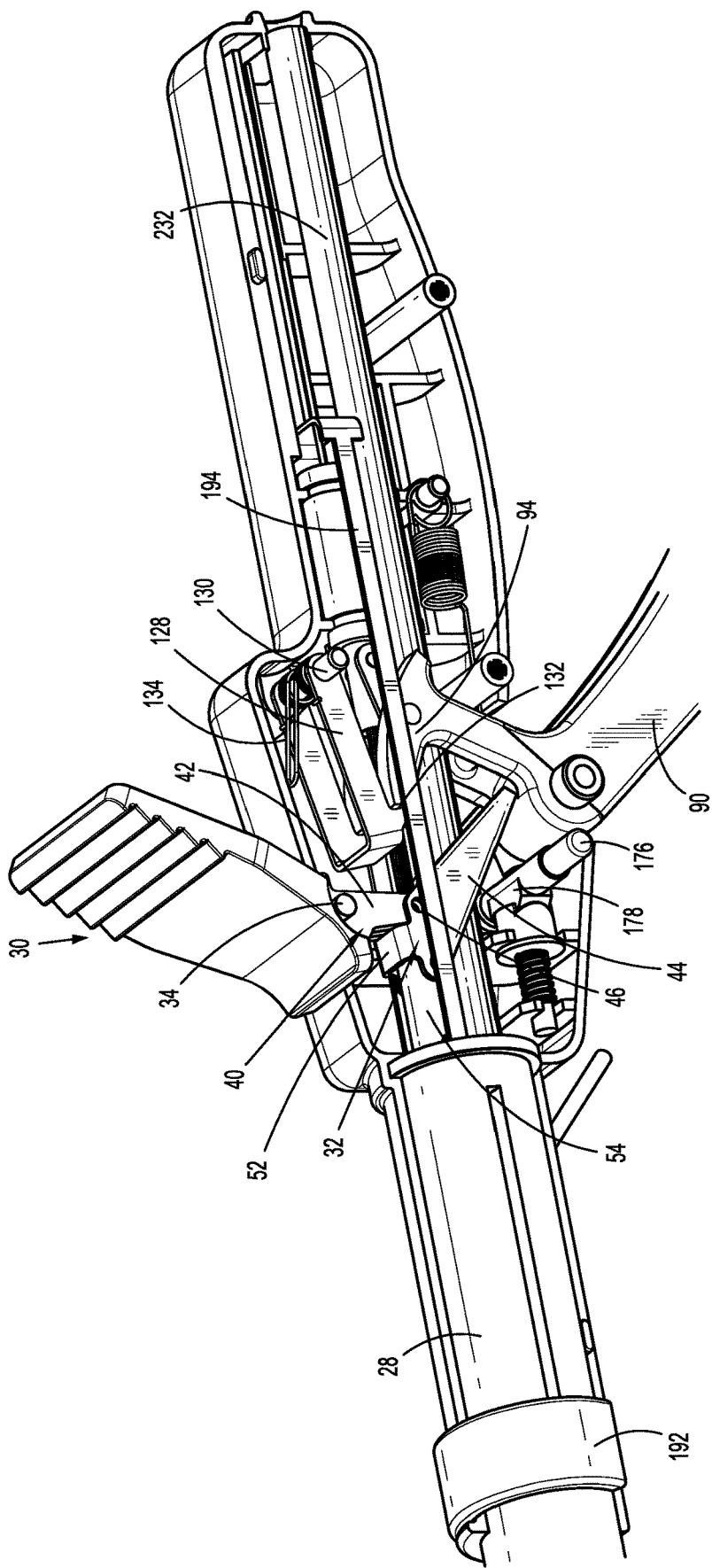
FIG. 6 is a perspective view of the handle of the surgical fastener apparatus with portions removed illustrating the handle prior to activation of the mechanisms.

With reference now to FIGS. 4-6, the approximator mechanism of the fastener apparatus 10 will be discussed. The approximator mechanism includes an approximator actuator 30 which is mounted to the handle frame 26 and an approximator link 32 coupled to the approximator actuator 30. The approximator actuator 30 may be pivotally mounted to the handle frame 26 through, e.g., reception of pivot pins 34 within corresponding pivot mounts 36 (FIGS. 1 and 4) within each of the frame half sections 26a. The approximator actuator 30 includes a manually engagable segment 38 disposed external of the handle frame 26 and a connector segment 40 which couples with the approximator link 32. In one embodiment, the connector segment 40 includes a pair of radially spaced legs 42 which are disposed within correspondingly dimensioned legs 44 of the approximator link 32 and secured via pin 46 extending through respective apertures 48, 50 of the legs 42, 44 (FIGS. 4 and 6). As best depicted in FIGS. 5 and 6, the approximator link 32 further includes a transverse drive shelf 52 extending between the legs 44. The drive shelf 52 is engaged by the spaced legs 42 of the approximator actuator 30 whereby pivotal movement of the approximator actuator 30 will cause corresponding longitudinal movement of the approximator link 32.

The approximator mechanism further includes a link collar 54 which is coupled to the approximator link 32 and an approximating tube 56 extending distally from the link collar 54. The link collar 54 is secured relative to the approximator link 32 through reception of pins 58 of the link collar 54 within apertures 60 of the approximator link 32 (FIG. 4). The approximating tube 56 is flexible and extends longitudinally through the elongate segment 14 for coupling with the end effector 16 as will be discussed The approximating tube 56 and the link collar 54 may be secured to each other via conventional means including adhesives, cements, fasteners or the like.

As best depicted in FIGS. 4 and 5, the approximator mechanism further includes a spring mechanism for biasing the link collar 54 in a proximal direction corresponding to an open condition of the end effector 16. The spring mechanism includes a spring stop 62 which is longitudinally fixed within the handle frame 26 and a spring 64. The spring 64, e.g., in the form of a coil spring, engages, at its distal end, a spring support wall 66 of the spring stop 62 and, at its proximal end, the distal flange segment 68 of the link collar 54 thereby normally biasing the link collar 54 in a proximal direction. This biased engagement causes the drive shelf 52 of the approximator link 32 to engage the connector segment 40 and rotate the approximator actuator 30 to the first or upright position of FIG. 5 (counter-clockwise with respect to FIG. 5) corresponding to the open condition of the end effector 16.

Figure 7:
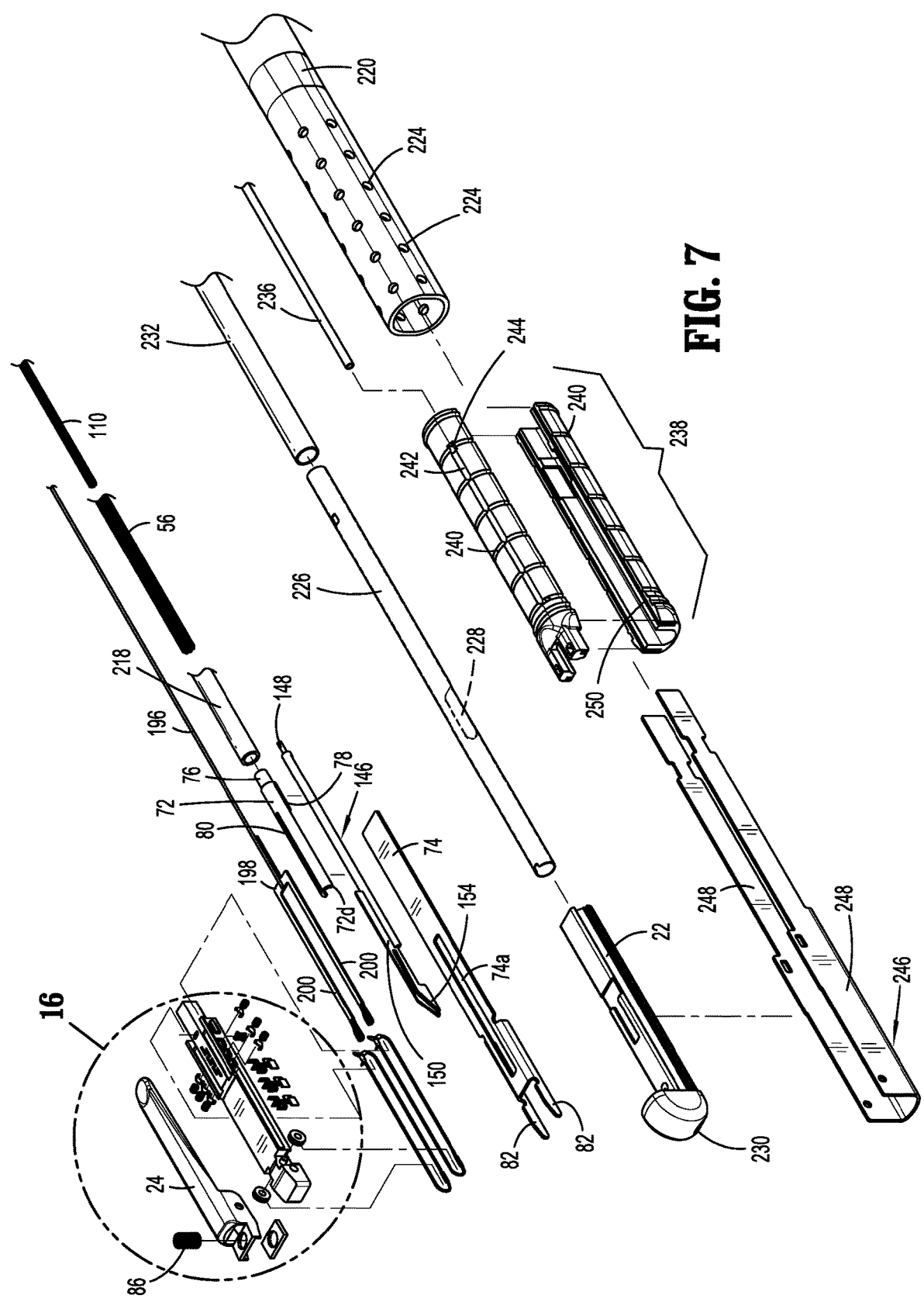
FIG. 7 is an exploded perspective view of the elongate segment of the surgical fastener apparatus.
Figure 8:
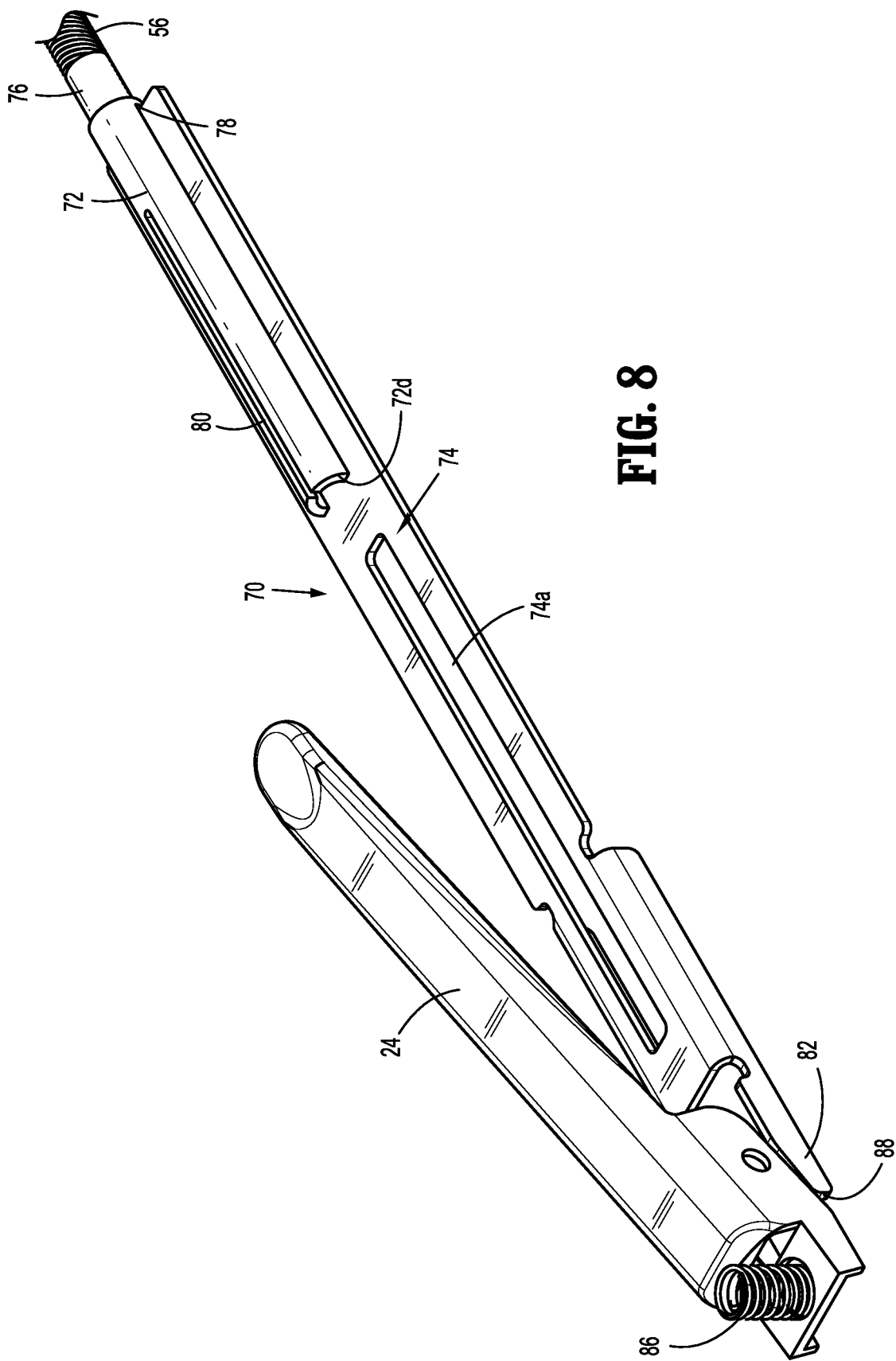
FIG. 8 is a perspective view of components of the approximator mechanism within the elongate segment for moving the end effector between the open and approximated conditions.

With reference now to FIGS. 7-8, further details of the approximator mechanism will be described. As discussed hereinabove, the approximating tube 56 is coupled, at its proximal end, to the link collar 54, which, in turn, is operatively coupled to the approximator actuator 30. The distal end of the approximating tube 56 is mounted to an approximator cam 70 which, in one embodiment, is inclusive of a cam link 72 and a cam drive 74. The cam link 72 includes a cylindrical proximal mounting section 76 to which the distal end of the approximating tube 56 is mounted and secured, e.g., through conventional methodologies. The cam drive 74 is secured to the cam link 72 by reception of the proximal end of the cam drive 74 within a recess 78 of the cam link 72 and/or with the use of adhesives (FIGS. 7 and 8). In the alternative, the cam link 72 and the cam drive 74 may be a single monolithic component. The distal segment of the cam link 72 is semi-circular in geometry and defines a recess or slot 80 extending through its distal end face 72d.

The cam drive 74 defines an internal slot 74a and has two laterally spaced cam bars 82 at its distal end. The cam bars 82 are engageable with the anvil 24 to cause pivoting movement of the anvil 24 relative to the fastener cartridge 22 of the end effector 16. As best depicted in FIGS. 9-10, the anvil 24 is mounted about a pivot pin 84 and is normally biased to the open condition by coil spring 86. The anvil 24 includes opposed cam surfaces 88 which are engaged by the cam bars 82 during longitudinal movement of the cam drive 74 to cause pivoting movement of the anvil 24 to the approximated condition as effected by manipulation of the approximator actuator 30.

Thus, the approximator mechanism is inclusive of the approximator actuator 30 and one or more approximator members (e.g., the approximating tube 56, cam link 72 and/or cam drive 74) where movement of the approximator actuator 30 causes longitudinal translation of the approximator member to thereby cause pivotal movement of the anvil 24 relative to the fastener cartridge 22.

Figure 11:
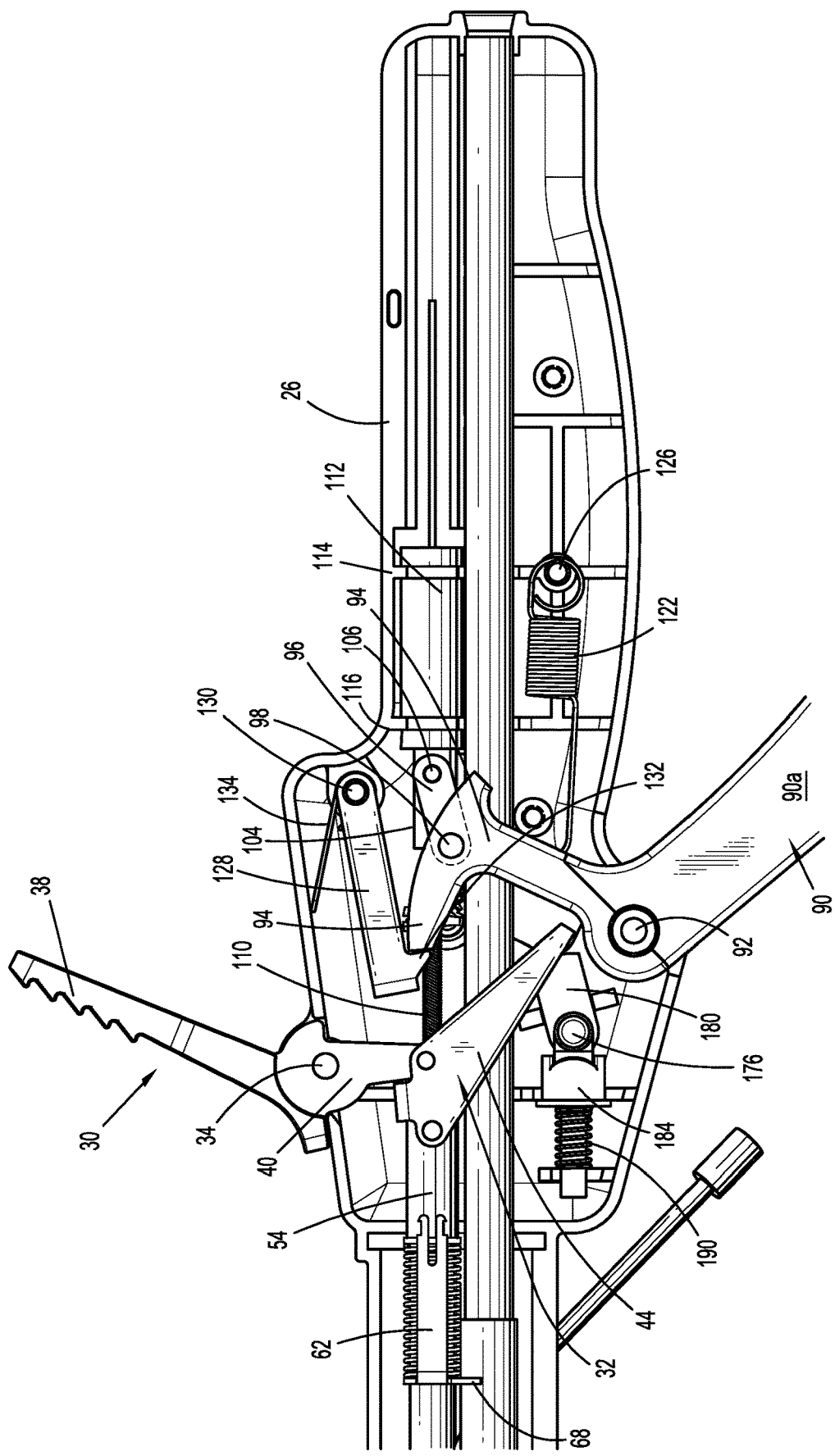
FIG. 11 is a side elevation view of the handle with portions of the handle frame removed illustrating components of the approximator mechanism and the fastener firing mechanism.

Referring initially now to FIG. 11, the fastener firing mechanism of the fastener apparatus 10 will be discussed. The fastener firing mechanism includes a firing trigger 90 which sequentially deploys fasteners from the end effector 16, i.e., the fastener cartridge 22 of the end effector 16. The firing trigger 90 is pivotally mounted about a pivot pin 92 coupled to the handle frame 26. The firing trigger 90 includes a manual engageable pistol grip 90a and a pair of laterally spaced firing arms 94 which are disposed within the interior of the handle frame 26. The firing arms 94 are coupled to a pair of firing links 96 via pin 98 extending through corresponding apertures 100, 102 of the firing arms 94 and the firing links 96, respectively (FIG. 4). The firing links 96 are coupled to a firing tube 104 through a pin 106 extending on each side of the firing tube 104 and received within apertures 108 of the firing links 96. (FIGS. 4 and 5) A firing sleeve 110 is received within the firing tube 104 and is secured therein with the use of adhesives, cements, etc. The firing sleeve 110 is flexible, and extends distally through the elongate segment 14, e.g., through the longitudinal bore of the approximating tube 56, as will be discussed. The firing sleeve 110 is received within a spacer 112 mounted within the handle frame 26 and traverses the spacer 112 during activation of the firing mechanism. The spacer 112 is mounted between internal walls 114, 116 of the handle frame 26.

The firing trigger 90 is biased toward its initial position by spring 122. One end of the spring 122 is coupled to a pin 124 extending between the firing arms 94 (FIG. 5) and the other end is secured to a pin 126 mounted within the handle frame 26. With this arrangement, the firing trigger 90 is normally biased in a clockwise direction (relative to FIG. 11) about the pivot pin 92 toward its initial position.

With continued reference to FIG. 11, the firing mechanism includes a trigger lockout within the handle frame 26 for locking the firing mechanism when the end effector 16 is in the open condition, or, otherwise stated, to prevent activation of the firing mechanism until the end effector 16 is in the approximated condition. The lockout includes a lock member 128 which is pivotally mounted within the handle frame 26 about a pivot pin 130. The lock member 128 includes a lock ledge 132 adjacent its distal end which engages the forward end of the firing arms 94 when in the first position of the approximator actuator 30. The lock member 128 is normally biased to the lock position of FIG. 11 via torsion spring 134 while the firing trigger 90 is biased via spring 122 to the initial position to position the firing arms 94 in engagement with the lock member 128. As will be described hereinbelow, pivotal movement of the approximator actuator 30 from the first position of FIG. 11 to the second position (FIG. 1) causes the approximator link 32 to pivot upwardly (in a counterclockwise direction with respect to FIG. 11) to engage and drive the lock member 128 in an upward direction (clockwise direction about pivot pin 130) to a release position displaced from the firing arms 94 thereby leaving the firing arms 94 unencumbered to advance in a distal direction.

Figure 12:
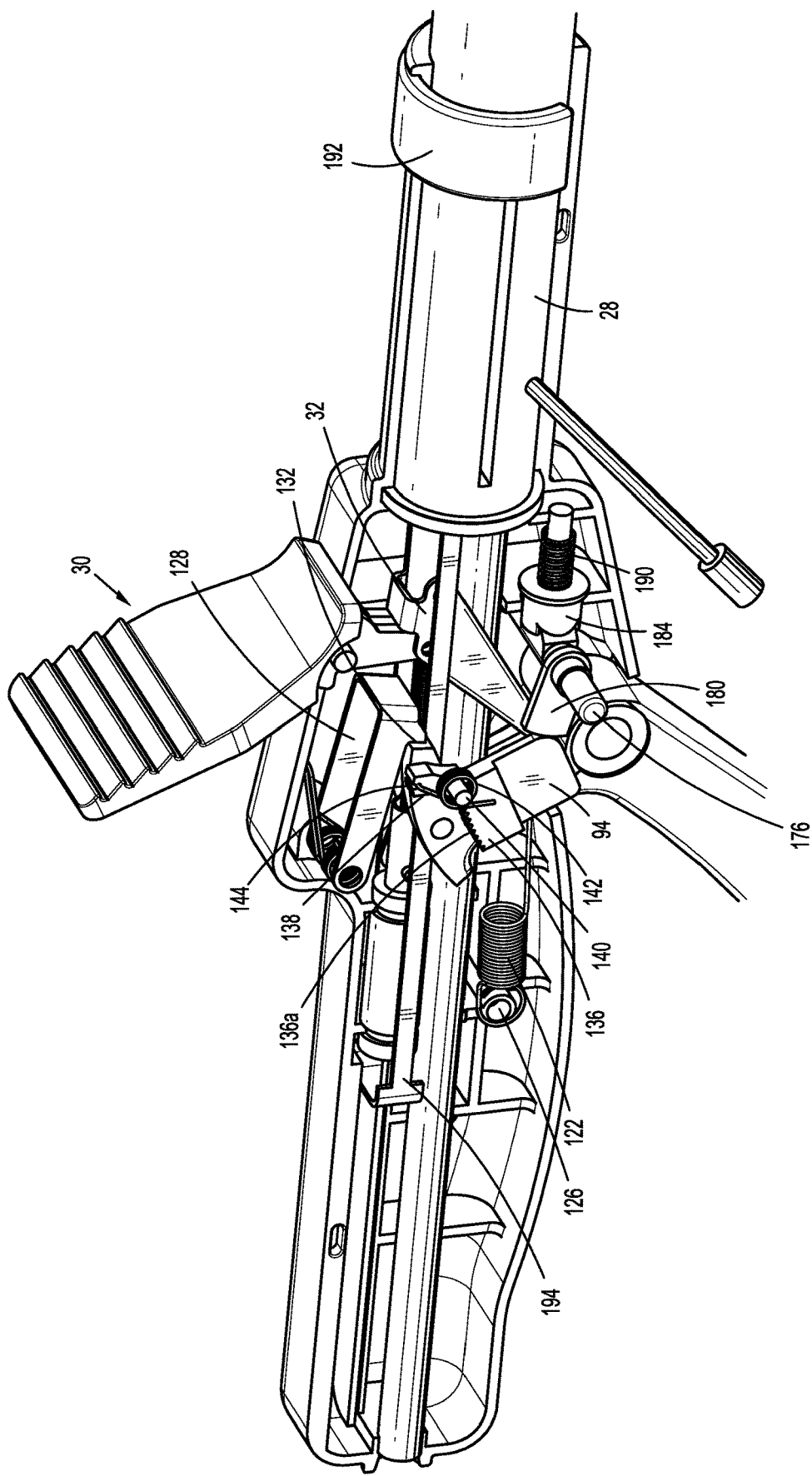
FIG. 12 is a perspective view of the handle with portions of the handle frame removed illustrating the ratchet mechanism of the approximator mechanism.

With reference to FIG. 12, the firing trigger 90 also includes a ratchet mechanism to permit selective incremental movement of the trigger 90 through a firing stroke between an initial position and a fully fired position, and/or to prevent movement of the firing trigger 90 towards its initial position once the firing stroke has commenced. The ratchet mechanism includes a ratchet 136 disposed on the rear side of one of the firing arms 94 of the firing trigger 90 and a pawl 138 which is pivotally mounted about a pin 140 to the handle frame 26. (See also FIG. 4) As best depicted in FIG. 12, the pawl 138 is spring biased into engagement with the teeth 136a of the ratchet 136 via a torsion spring 142 which is also mounted about the pin 140. One end of the torsion spring 142 is accommodated within an upper recess 144 of the pawl 138 and the second end is received within a recess (not shown) of the handle frame 26.

With reference now to FIGS. 13-14, the firing sleeve 110 is operatively coupled to the firing trigger 90 and extends longitudinally through the flexible elongate segment 14. The distal end of the firing sleeve 110 is coupled to a firing cam 146. The firing cam 146 includes a cylindrical segment 148 having a reduced cross-section at its proximal end segment about which the firing sleeve 110 is positioned and secured. The distal end 150 of the firing cam 146 has a slot or groove 152 which extends through its distal face. The slot 152 defines a distal angled segment 152a obliquely arranged with respect to the longitudinal axis "k" and a proximal segment 152b parallel to the longitudinal axis "k". The distal angled segment 152a defines an inner cam surface 154. The distal end 150 of the firing cam 146 may be substantially planar and is at least partially accommodated within the internal slot 74a of the cam drive 74 and the slot 80 of the cam link 72 (see FIG. 7) and traverses these slots 74a, 80 during the firing stroke.

Figure 15:
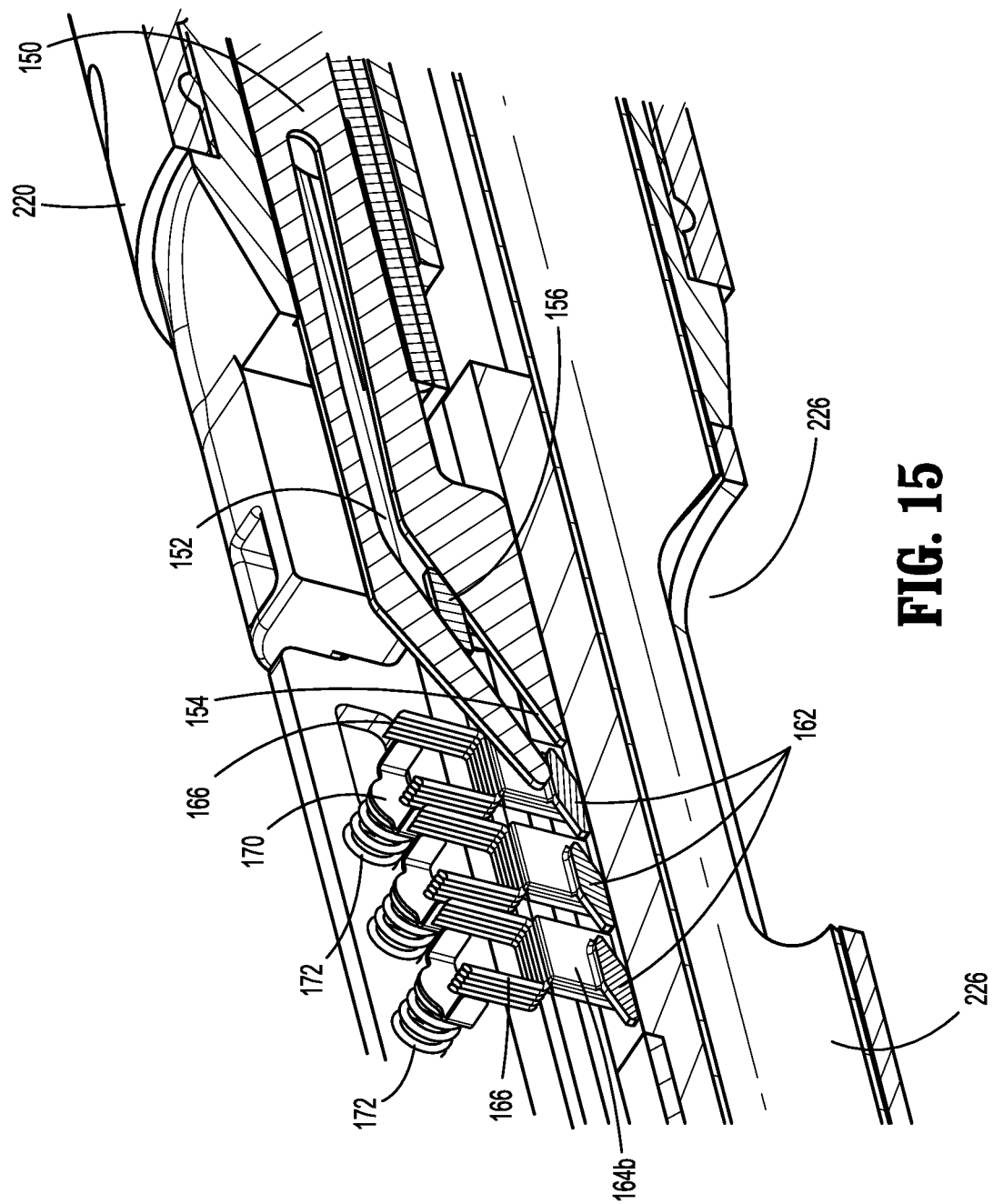
FIG. 15 is an enlarged perspective view with portions removed illustrating the components of the fastener firing mechanism within the fastener cartridge.
Figure 16:
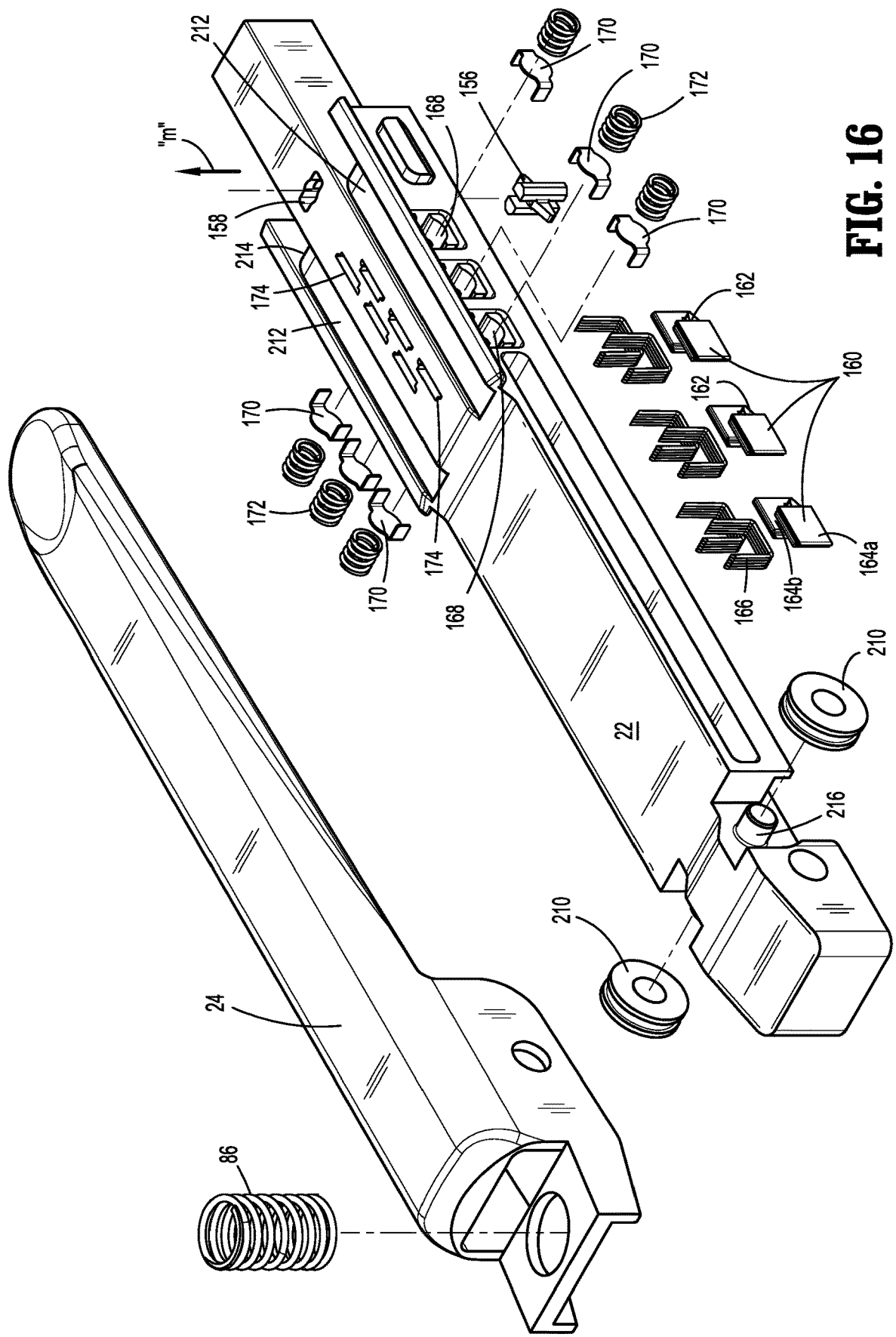
FIG. 16 is an exploded perspective view of the area of detail identified in FIG. 7 illustrating the components of the fastener firing mechanism within the fastener cartridge.

With reference to FIGS. 14-16, further details of the fastener firing mechanism and the fastener cartridge 22 will be described. The firing cam 146 includes a separator 156 disposed within the slot 152 of the firing cam 146 to maintain the spacing or dimensioning of the slot 152 during longitudinal traversing movement of the firing cam 146 through the fastener cartridge 22 during the firing stroke. The separator 156 is disposed within a separator mount or recess 158 defined in the fastener cartridge 22 and can traverse the separator recess 158 in a direction "m" transverse, e.g., orthogonal, to the longitudinal axis "k" as it traverses the slot 152 in the firing cam 146 (FIG. 16). The inner cam surface 154 of the firing cam 146 engages a plurality of pushers 160 disposed within the fastener cartridge 22. The pushers 160 include pusher cams 162 which traverse the slot 152 within the firing cam 146 during longitudinal movement of the firing cam 146, e.g., during firing of the apparatus 10, to drive the pushers 160 in the direction "m". The pushers 160 include opposed pusher plates 164a, 164b interconnected by the pusher cams 162.

The fastener cartridge 22 includes a plurality, e.g., two laterally spaced rows of fasteners, e.g., staples 166, which are arranged in staggered or longitudinally spaced relation with respect to the longitudinal axis "k". In one embodiment, each row includes three sets of fasteners 166 with each set having three or more (e.g., four) individual fasteners 166. The pushers 160 are arranged to engage adjacent sets of fasteners 166 of the rows with each individual plate 164a, 164b of the pushers 160 contacting longitudinally adjacent sets of the respective rows. As best depicted in FIG. 16, the fasteners 166 of each set are received within the fastener holding receptacles 168 defined within the fastener cartridge 22. A pressure plate 170 is positioned within each fastener holding receptacles 168 and is biased into engagement with the fasteners 166 by a coil spring 172. The spring bias of the pressure plates 170 positions the fasteners 166 into alignment with respective plates 164a, 164b of the pushers 160 and into alignment with the outlet openings 174 of the fastener holding receptacles 168 (FIG. 16).

Figure 17:
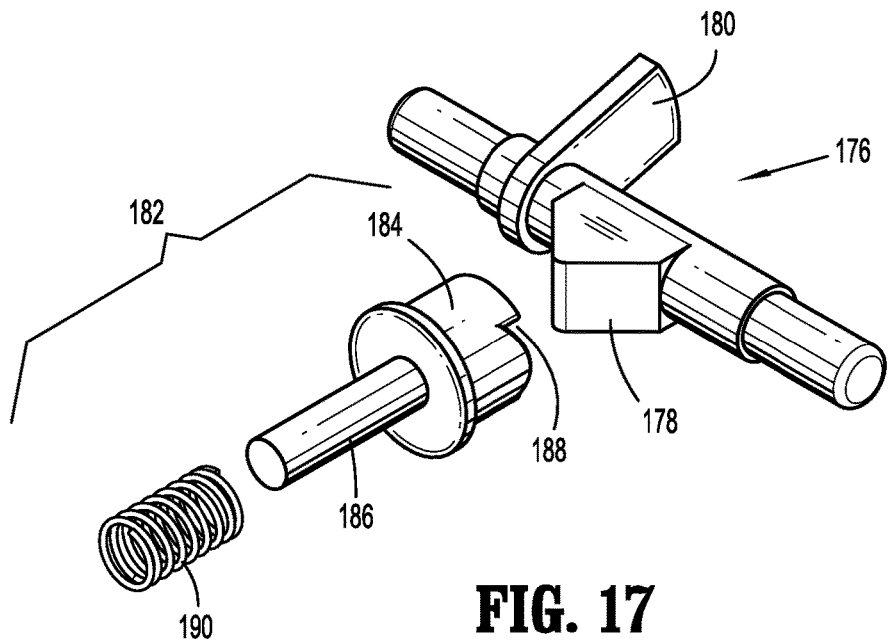
FIG. 17 is an exploded perspective view of the components of the safety mechanism for preventing firing of the firing mechanism.

Referring now to FIGS. 12 and 17, the fastener apparatus 10 also includes a safety for preventing firing of the firing mechanism until the operator is prepared to commence the fastening procedure and apply the fasteners 166. The safety includes a manually engageable safety member or button 176 which at least partially extends outwardly from the handle frame 26 of the firing apparatus 10. The safety button 176 is adapted for reciprocal motion both radially inwardly and outwardly relative to the handle frame 26. The safety button 176 includes a safety wedge segment 178 and a firing lock segment 180 depending proximally toward the firing arms 94. A safety biasing member 182 engages the wedge segment 178 of the safety button 176. The safety biasing member 182 includes a wedge receptacle 184 and a pin 186 depending from the wedge receptacle 184. The wedge receptacle 184 defines a wedge recess 188 correspondingly dimensioned to receive the wedge segment 178 of the safety button 176 and is normally biased to the secured position of FIG. 12 by a coil spring 190 which is mounted about the pin 186 and engages an internal wall of the handle frame 26 (FIG. 5). In the secured position of the safety button 176, the firing lock segment 180 engages one of the firing arms 94, e.g., the firing arm with the ratchet 136 as best depicted in FIG. 12. This engagement prevents movement of the firing arms 94 in the distal direction. In operation, depression of the safety button 176 radially inwardly causes the wedge segment 178 to disengage from the wedge receptacle 184 of the safety biasing member 182, and also causes the firing lock segment 180 to laterally displace and disengage from the firing arm 94 thereby permitting the firing arms 94 to move in a distal driving direction.

Figure 18:
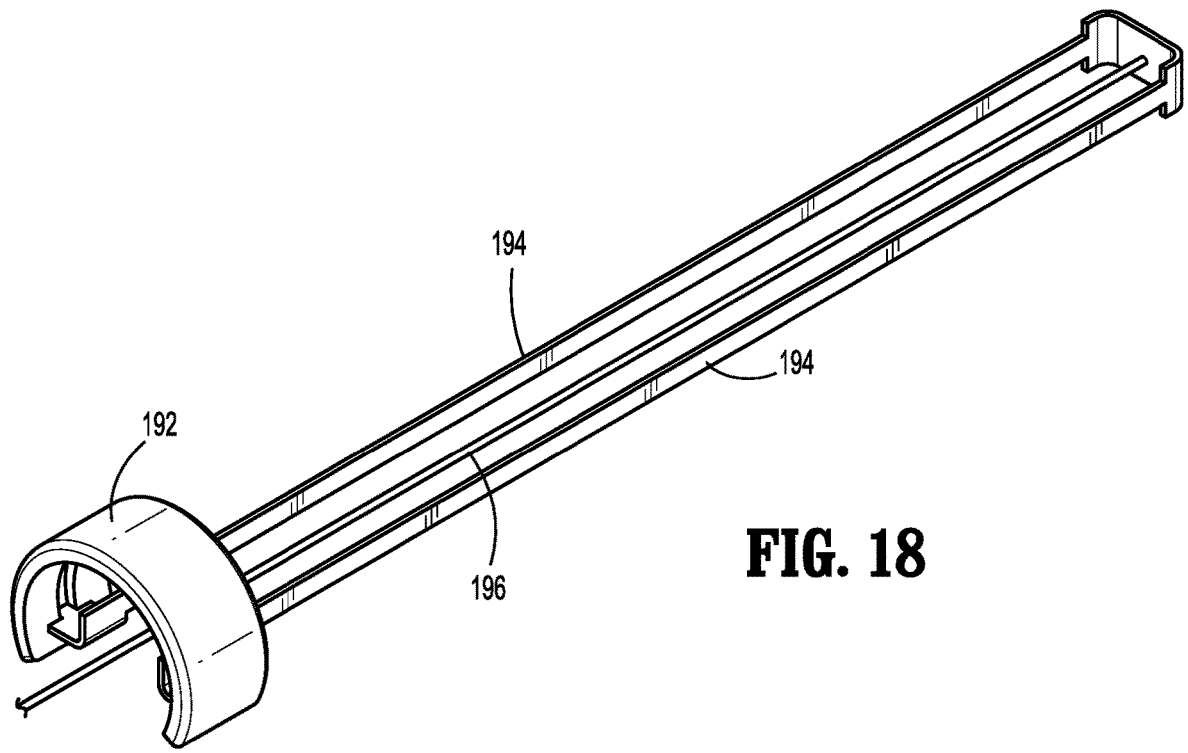
FIG. 18 is a perspective view illustrating components of the tissue grasping mechanism within the handle.

Referring now to FIG. 18, the tissue grasper mechanism for pulling tissue, e.g. gastric and esophageal tissue, within the end effector 16 will be described. The tissue grasper mechanism includes a manually operable grasper actuator or slider 192 mounted to the forward cylindrical segment 28 of the handle frame 26, a tissue grasper frame 194 secured to the grasper actuator 192 and a grasper rod 196 each disposed within the handle frame 26. (FIG. 12) The grasper rod 196 is secured to the grasper frame 194 and thus is operatively coupled to the grasper actuator 192. The grasper actuator 192 is adapted for reciprocal longitudinal movement along or relative to the forward cylindrical segment 28 to cause corresponding reciprocal movement of the grasper rod 196.

With reference now to FIGS. 19-21, the grasper rod 196 extends distally through the elongate segment 14, e.g., through the longitudinal bore of the firing sleeve 110, and is secured to a grasper drive member 198 which is mounted at least partially within the fastener cartridge 22. As best depicted in FIG. 19, the grasper drive member 198 includes two depending legs 200 laterally or radially spaced relative to each other with each of the depending legs 200 having connector segments 202 at their distal ends. The tissue grasper mechanism further includes two grasper pulley mechanisms 204. Each grasper pulley mechanism 204 includes a closed loop member 206, a tissue grasper 208 secured to the closed loop member 206 and a pulley 210. The closed loop member 206 may be any cable, wire, rod or string having sufficient flexibility to extend about the pulley 210. The closed loop members 206 are each looped about a respective pulley 210 and about the fastener cartridge 22, and are secured to the connector segments 202 of the grasper drive member 198. In one embodiment, the fastener cartridge 22 includes guide grooves 212 for accommodating portions of the closed loop members 206. The guide grooves 212 extend between opposed surfaces of the fastener cartridge 22 and have arcuate guide turns 214 adjacent the proximal end of the fastener cartridge 22. (See also FIG. 16) Each closed loop member 206 and attached tissue grasper 208 reciprocally moves relative to the longitudinal axis "k" along the path defined between the pulleys 210 and the guide turns 214 of the fastener cartridge 22 during corresponding longitudinal movement of the grasper drive member 198. In particular, with reference to FIG. 21, each closed loop member 206 and tissue grasper 208 longitudinally move in a distal direction toward the pulleys 210 upon retracting movement of the grasper drive member 198, the grasper rod 196 and the grasper actuator 192. The pulleys 210 are mounted for rotation to the fastener cartridge 22 by pins or axles 216. (FIG. 16).

As shown in FIG. 22, the tissue graspers 208 are secured to the closed loop members 206 via conventional means. The tissue graspers 208 each include first and second grasper prongs 208a, 208b which extend at opposite angles to facilitate engagement with tissue regardless of the orientation of the end effector 16. The grasper prongs 208a, 208b may be sharp to penetrate tissue or dimensioned to engage the tissue with minimal penetration. The provision of multiple pulley mechanisms 204 and attached laterally spaced tissue graspers 208 ensures a sufficient volume of tissue, e.g., gastric and esophageal tissue, is drawn between the end effector 16 thereby enhancing the tissue fastening process.

Figures 23, 24:
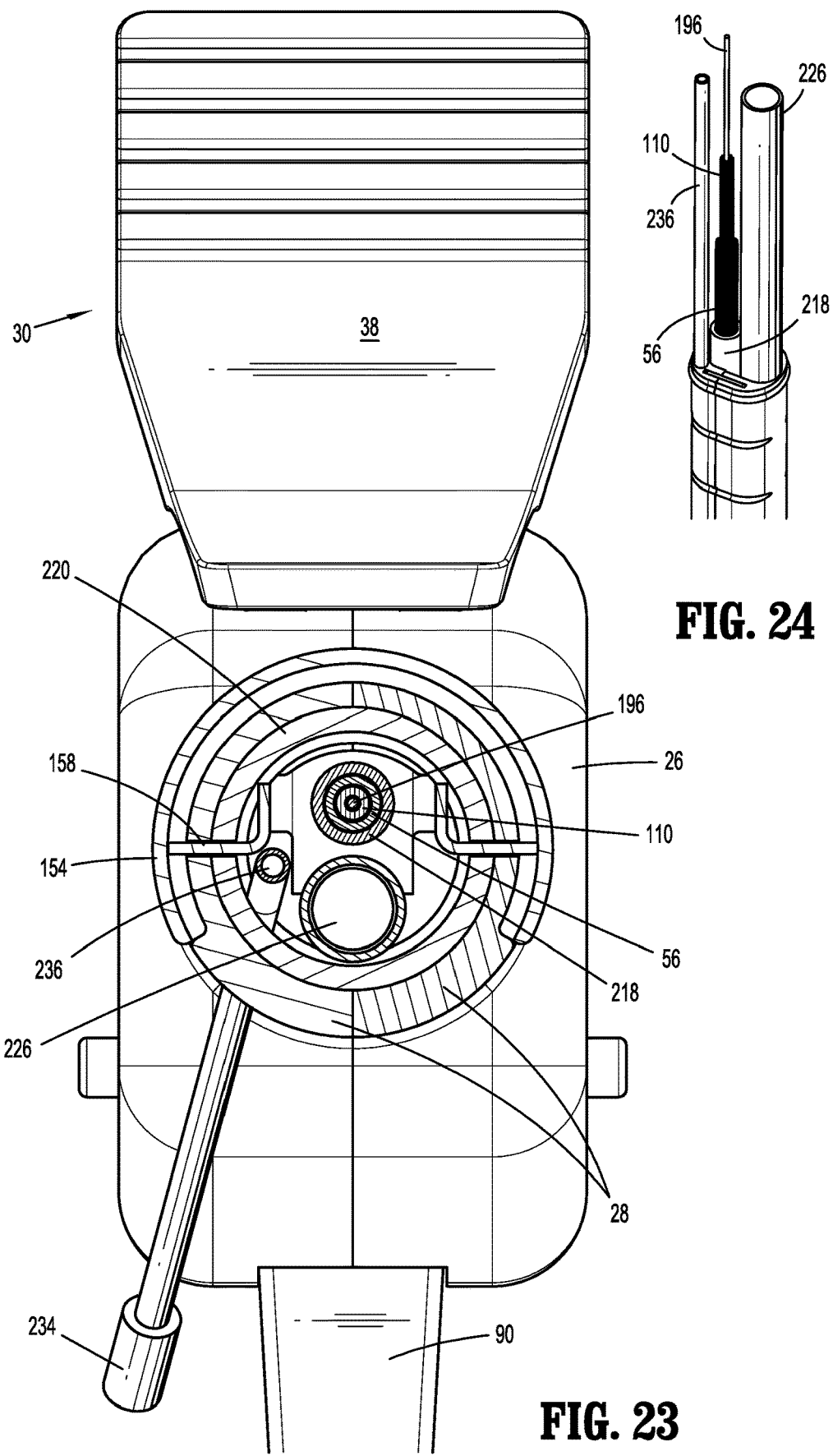
FIG. 23 is a cross-sectional view taken along the lines 23-23 of FIG. 5.
FIG. 24 is a perspective view illustrating components of the elongate segment including the outer sleeve, vacuum tube and the scope channel.

Referring now to FIGS. 23-24, the elongate segment 14 further includes a central tube 218 which encloses the approximating tube 56, the firing sleeve 110 and the grasper rod 196 (see also FIG. 7). The central tube 218 is received within an aperture 62a of the spring stop 62 (FIG. 4) and is secured relative to the handle frame 26 via conventional means, e.g., through direct securement to the spring stop 62 or to the handle frame 26. Each of the approximating tube 56, the firing sleeve 110 and the grasper rod 196 are capable of longitudinal traversing movement within the central tube 218.

The elongate segment 14 further includes an outer tube 220 which encloses the central tube 218 and the remaining components of the elongate segment 14. The outer tube 220 is flexible and may be fabricated from any suitable polymeric material. The outer tube 220 may include a proximal collar 222 (FIG. 5) for reception within an annular recess within the handle frame 26 to secure the outer tube 220 relative to the handle 12. The outer tube 220 includes a plurality of vacuum apertures 224 adjacent its distal end and extending completely through the tube wall for conveying a vacuum or negative pressure (FIGS. 1 and 7).

With continued reference to FIGS. 23-24, the elongate segment 14 further includes a scope channel or tube 226 extending through the elongate segment 14 for reception of an endoscope. The scope tube 226 includes a laterally faced visualization window 228 for permitting lateral viewing of the procedure with the endoscope (FIGS. 9 and 14). The scope tube 226 extends through the fastener cartridge 22 and is in communication with a scope exit opening 230 within the fastener cartridge 22. The scope tube 226 is in communication with a scope sleeve or bore 232 at least partially extending through the handle frame 26. (FIG. 6)

Referring now to FIGS. 25-26, the vacuum mechanism for drawing tissue toward the elongate segment 14 to facilitate securing of the elongate segment 14 within tissue, e.g., the esophagus will be described. The vacuum mechanism includes a vacuum connector 234 mounted adjacent the handle frame 26 and connectable to a vacuum source "vs", and communicates with a vacuum conduit or tube 236 (FIGS. 4 and 7). The vacuum tube 236 extends within the outer tube 220 of the elongate segment 14 disposed external of the central tube 218. The vacuum tube 236 is in communication with a vacuum distributor 238 which is mounted within the outer tube 220. The vacuum distributor 238 defines a plurality of annular and longitudinal grooves 240, 242 in its outer wall which are in communication with the vacuum tube 236 via distributor inlet 244 extending through the wall of the vacuum distributor 238. The annular and longitudinal grooves 240, 242 communicate with the vacuum apertures 224 in the outer tube 220 to subject tissue to vacuum or negative pressure during the procedure, which assists in securing the elongate segment 14 relative to tissue, e.g., the esophageal tract. The vacuum distributor 238 is secured relative to the fastener cartridge 22 via connector 246 (FIG. 7). The connector 246 may include connector arms 248 which are received within longitudinal mount grooves 250 of the vacuum distributor 238 to secure the connector 246 relative to the vacuum distributor 238. The connector 246 may be secured to the fastener cartridge 22 via conventional methodologies.

Figure 27:
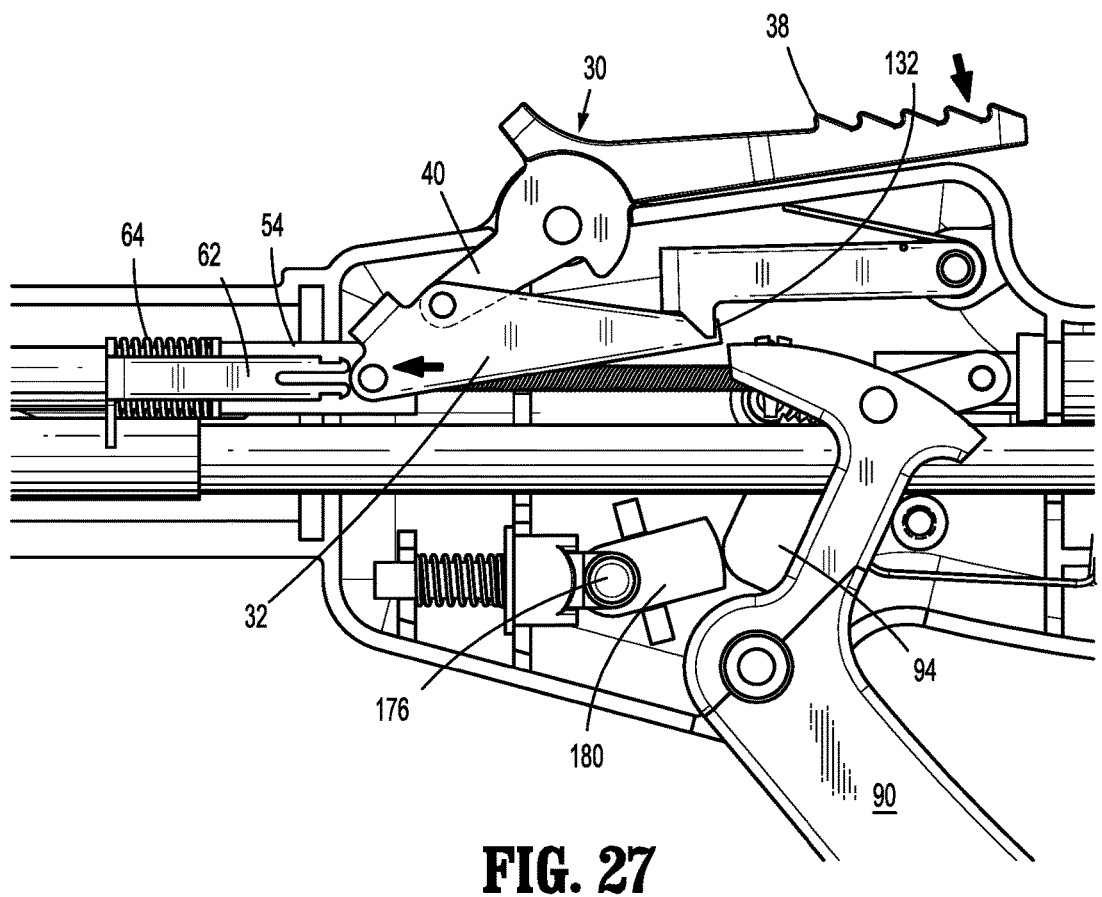
FIG. 27 is a side elevation view of the handle with portions of the handle frame removed illustrating the approximator actuator moved from a first position to a second position corresponding to the approximated condition of the anvil relative to the fastener cartridge.
Figure 28:
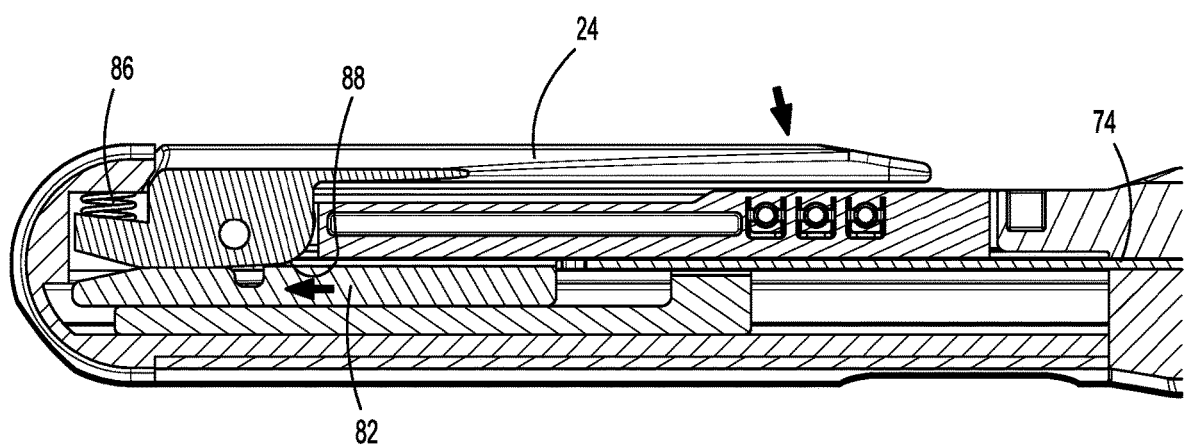
FIG. 28 is a side cross-sectional view illustrating the end effector in the approximated condition.

The use of the fastener apparatus 10 in conjunction with the performance of a transoral incisionless fundoplication (TIF) procedure will now be discussed. Referring now to FIG. 27, the approximator actuator 30 is pivoted in a clockwise direction (relative to FIG. 27) from its first position to its second position through engagement with the manually engageable segment 38 which causes the connector segment 40 to correspondingly pivot and longitudinally drive the approximator link 32 in a distal direction. The distal advancing movement of the approximator link 32 causes corresponding movement of the link collar 54 against the bias of the spring 64 and movement of the attached approximating tube 56, the cam link 72 and the cam drive 74 which are secured to the approximating tube 56. In the second position of the approximator actuator 30, the approximator link 32 and the approximator actuator 30 are in general longitudinal alignment with the spring 64 whereby the longitudinally directed biasing forces of the spring 64 maintain the approximator actuator 30 in the second position. As best depicted in FIG. 28, the distal advancing movement of the cam drive 74 effects engagement of the cam bars 82 of the cam drive 74 with the cam surfaces 88 of the anvil 24 to pivot the anvil 24 to the closed or approximated condition against the bias of spring 86. The firing lock segment 180 of the safety button 176 is in engagement with the firing arm 94 preventing inadvertent firing of the firing mechanism.

Figure 29:
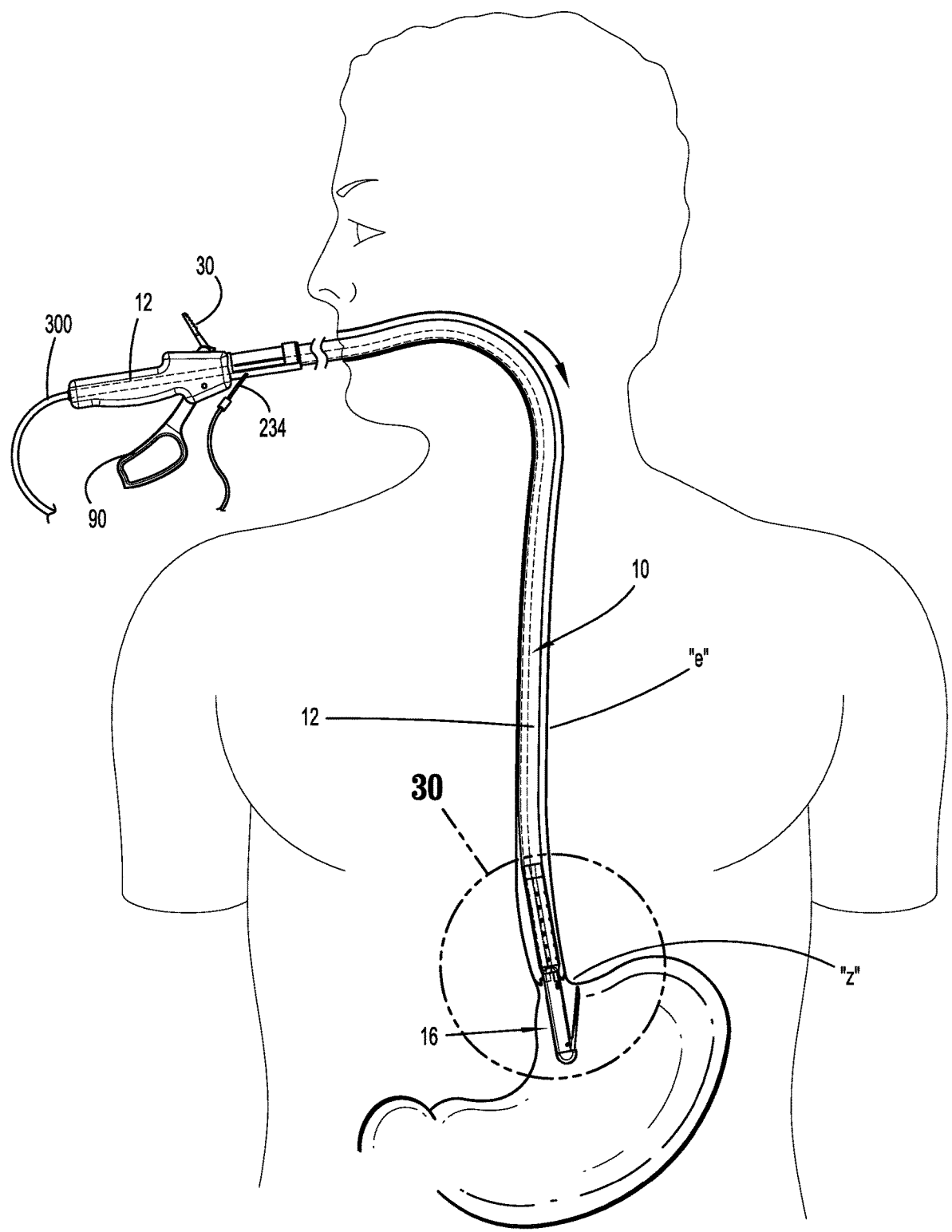
FIG. 29 is a view illustrating insertion of the fastener firing apparatus and an endoscope within the esophageal tract of a patient.
Figure 30:
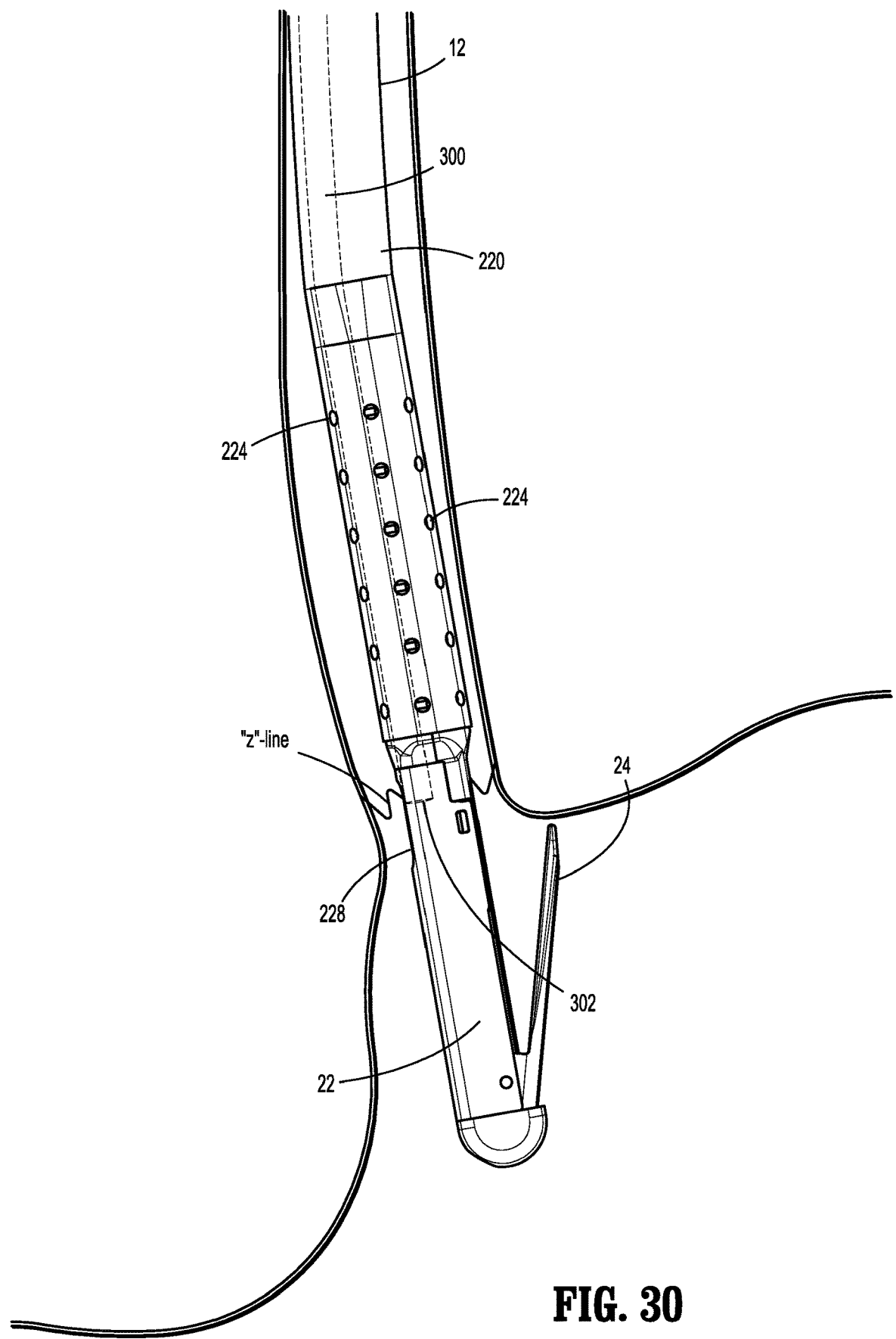
FIG. 30 is an enlarged isolated view of the area of detail identified in FIG. 29 illustrating the end effector positioned within the stomach of the patient.

Referring now to FIGS. 29-30, an endoscope 300 is positioned within the scope tube 226 of the fastener apparatus 10 and advanced to orient the optical window 302 of the endoscope 300 adjacent the visualization window 228 of the scope tube 226. With the end effector 16 in the approximated condition, the fastener apparatus 10 and the endoscope 300 are advanced along the esophageal tract "e" until the end effector 16 is adjacent the Z-line "z", i.e., the junction of the esophageal and the gastric mucosa as visually confirmed by viewing with the endoscope 300 through the visualization window 228. In the alternative, the endoscope 300 may be advanced within the esophageal tract "e" and the fastener apparatus 10 subsequently slid along the endoscope 300 via entry of the endoscope 300 within the scope tube 226. The end effector 16 is then moved to the open condition via release or manipulation of the approximator actuator 30 (to assume its first position) such that the anvil 24 is spaced from the fastener cartridge 22 as depicted in FIG. 30.

Figure 31:
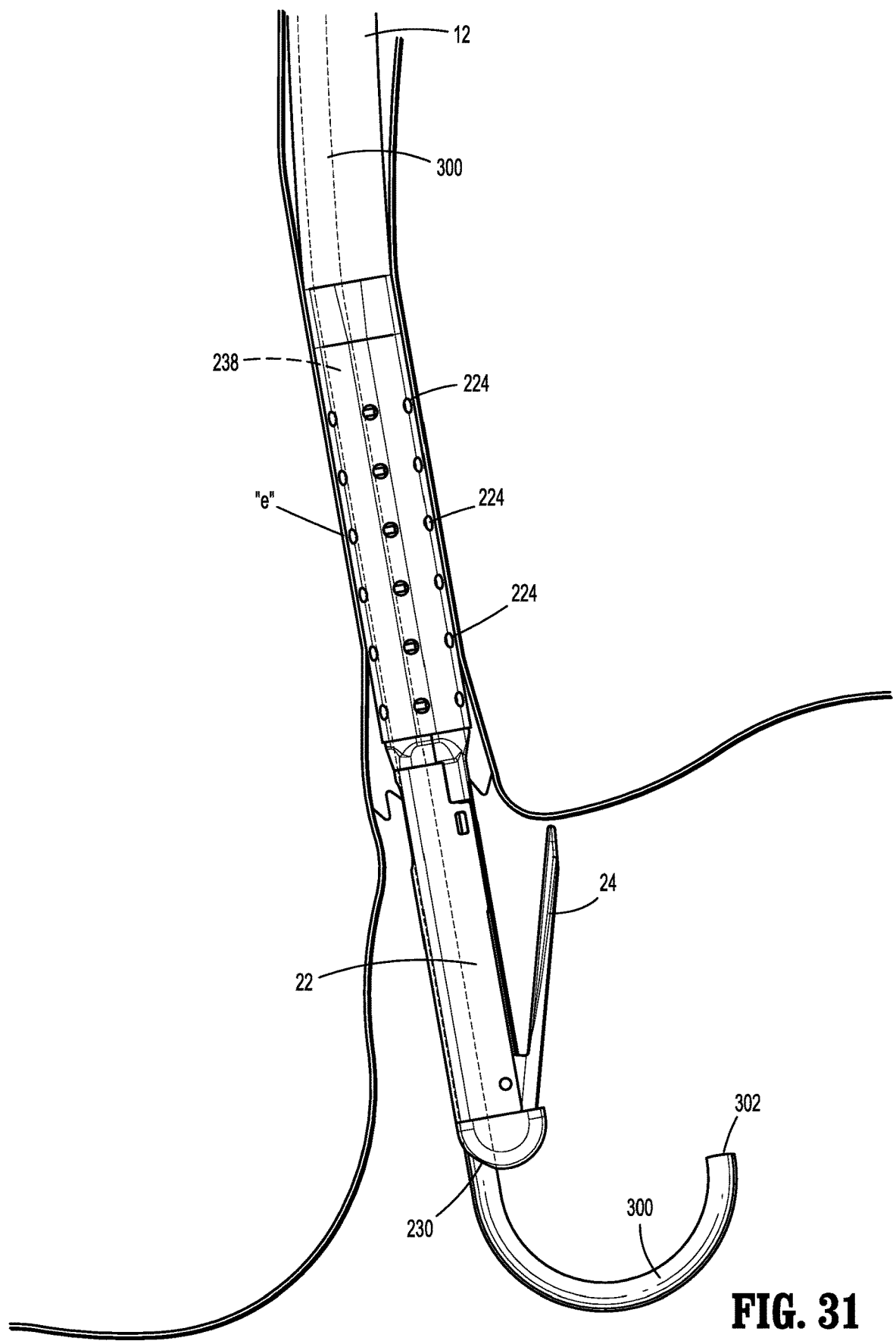
FIG. 31 is a view of the esophageal tract upon activation of the vacuum system to draw the esophageal wall upon the elongate segment and also depicting the endoscope deployed from the surgical fastener apparatus.

With reference to FIG. 31, a vacuum is coupled to the vacuum connector 234 and a vacuum is drawn through the vacuum tube 236 and the vacuum distributor 238. The vacuum or negative pressure is conveyed through the annular and longitudinal grooves 240, 242 of the vacuum distributor 238 and through the vacuum apertures 224 in the outer tube 220 to draw the esophageal tissue against the elongate segment 14 thereby securing the fastener apparatus 10 relative to the esophageal tract "e". The endoscope 300 is extended through the scope exit opening 230 of the fastener cartridge 22 and oriented to face in the general direction of the Z-line "z".

Figure 32:
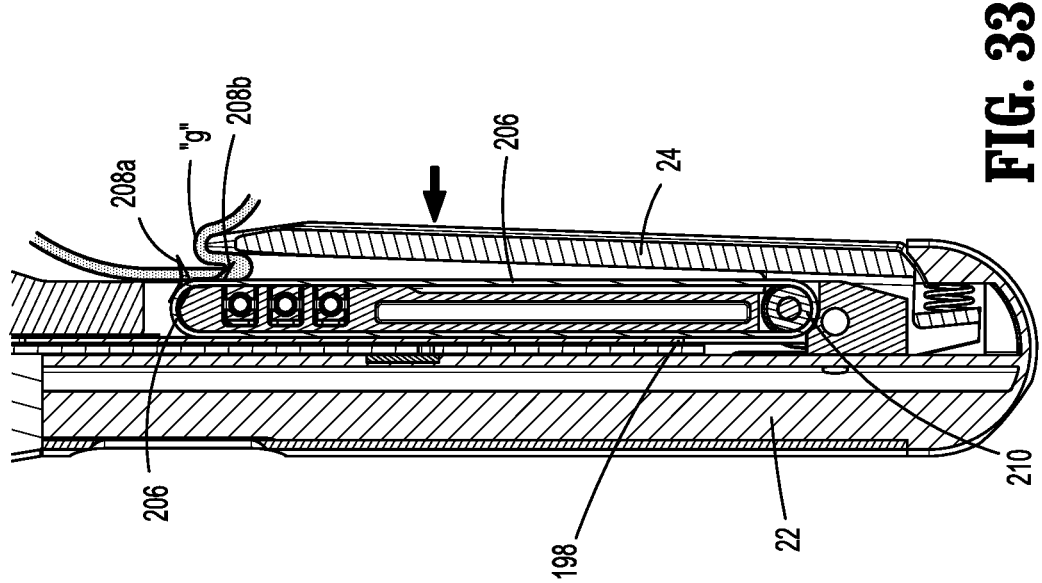
FIGS. 32-33 are views illustrating the anvil of the end effector in the open and approximated conditions, respectively, to engage a portion of the stomach or gastric tissue.
Figure 33:
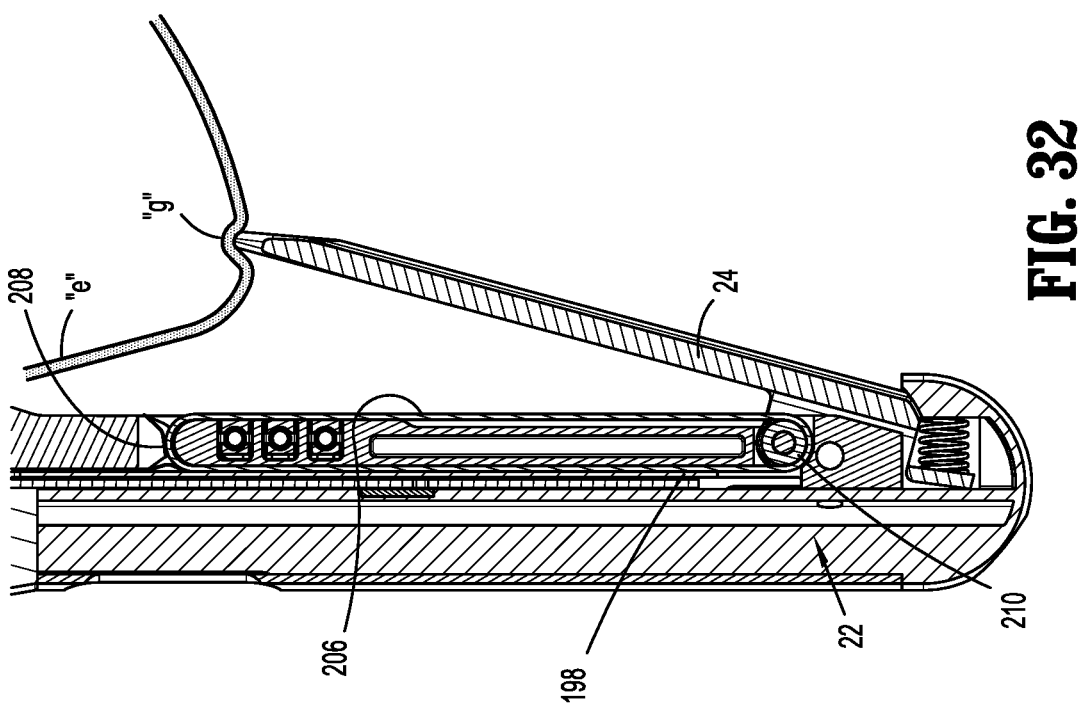

Referring now to FIG. 32, with the vacuum or negative pressure still applied, the fastener apparatus 10 is pulled slightly toward the clinician such that the tip of the open anvil 24 engages gastric tissue "g". The anvil 24 is moved to the approximated condition through manipulation of the approximator actuator 30 capturing a portion of the gastric tissue "g" between the anvil 24 and the fastener cartridge 22 as depicted in FIG. 33. Thereafter, the tissue grasper mechanism may be actuated by sliding the grasper actuator 192 along the forward cylindrical segment 28 of the handle frame 26 in a proximal direction for an initial predetermined distance, e.g., to a first actuated position, as depicted in FIG. 34. This causes the grasper drive member 198 to move in a proximal direction thereby causing the closed loop members 206 to begin rotating. Rotation of the closed loop members 206 (which are secured to the grasper member 198 via the connector segments 202) moves the attached tissue graspers 208 in a distal direction whereby the tissue graspers 208 initially engage and/or penetrate the gastric tissue "g" as shown in FIG. 33.

With reference to FIG. 35, the end effector 16 is again moved to the open condition by releasing the approximator actuator 30 which thus rotates in to its first upright position (FIG. 12) under the influence of spring 64, and causes proximal movement of the approximating tube 56, the cam link 72 and the cam drive 74. Thereafter, the grasper actuator or slider 192 of the tissue grasper mechanism is moved from the first actuated position of FIG. 34 along the forward cylindrical segment 28 of the handle frame 26 in a proximal direction, which continually draws the grasper rod 196 and the grasper frame 194 in a proximal direction. This movement activates the grasper pulley mechanisms 204 to cause the closed loop members 206 to revolve (directional arrow "r") within the fastener cartridge whereby the tissue graspers 208 move in a distal direction thereby drawing the gastric tissue "g" and esophageal tissue "et" in a distal direction within the open end effector 16 as depicted in FIG. 35.

Figure 36:
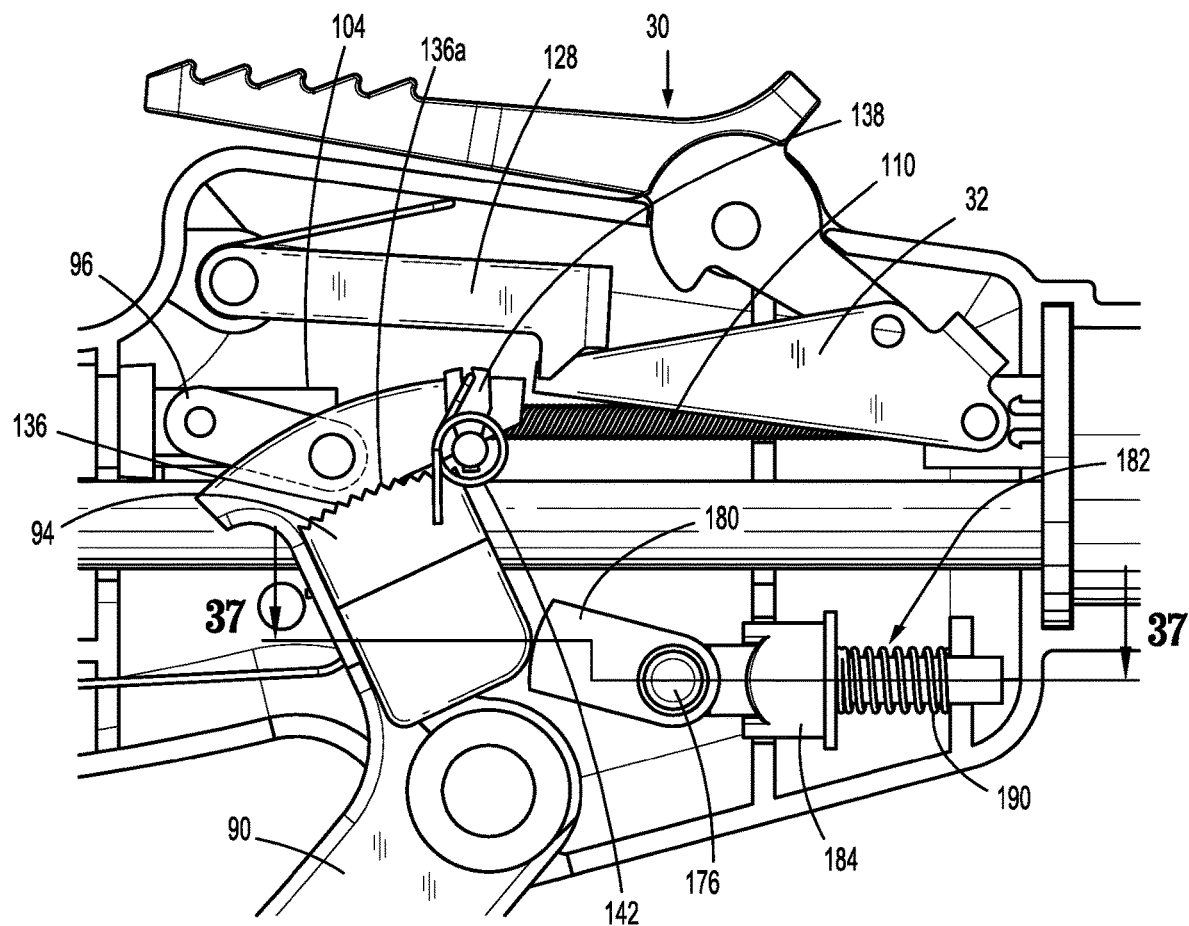
FIG. 36 is an enlarged side elevation view of the handle with portions of the handle frame removed illustrating the ratchet mechanism prior to activation of the firing mechanism.
Figure 37:
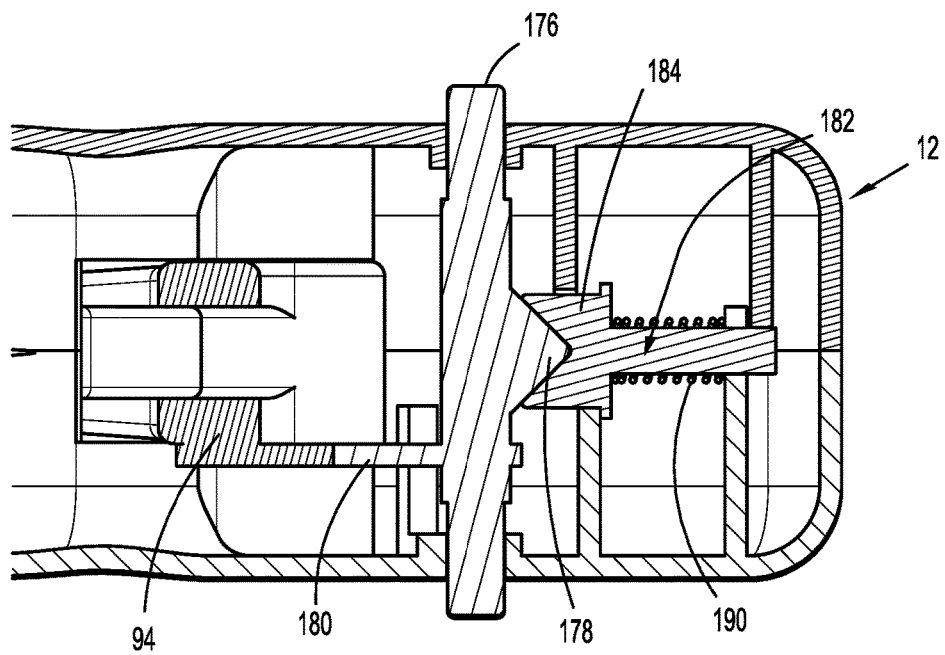
FIG. 37 is a cross-sectional view taken along the lines 37-37 of FIG. 36 illustrating the safety button in the secured position prior to activation of the firing mechanism.
Figure 38:
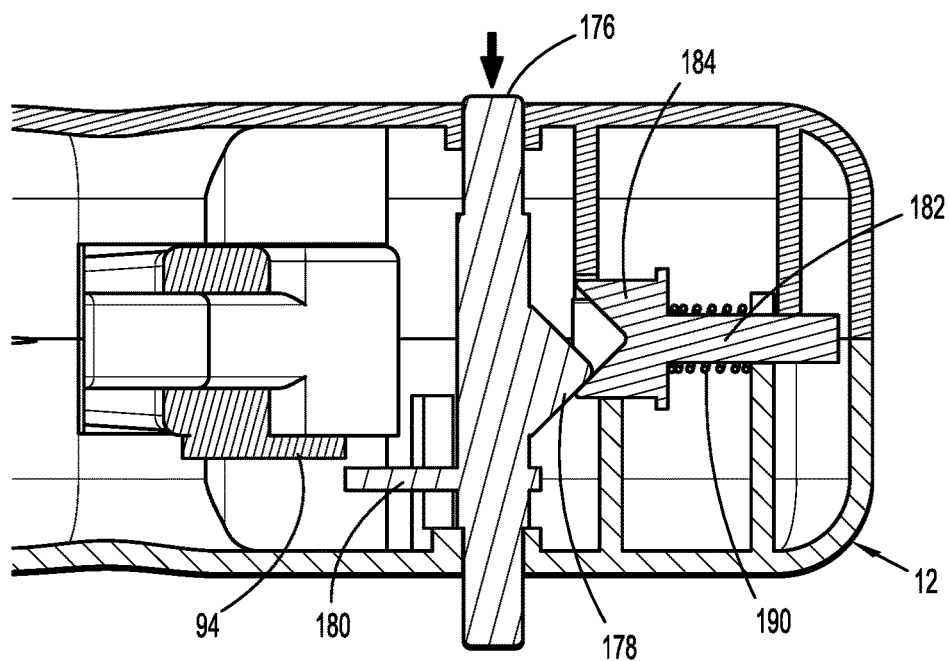
FIG. 38 is a view similar to the view of FIG. 37 illustrating the safety button in an unsecured position.

Referring now to FIGS. 36-37, the approximator actuator 30 is then rotated to its second position to move the anvil 24 to the approximated condition relative to the fastener cartridge 22. As discussed in detail hereinabove, this movement also causes the approximator link 32 to pivot upwardly, which drives the lock member 128 in an upward direction to a release position releasing the firing arms 94. At this point in the procedure, the firing mechanism is incapable of being activated through the positioning of the safety button 176. In particular, the firing lock segment 180 of the safety button 176 engages the firing arm 94, e.g., the firing arm 94 with the ratchet 136, to prevent movement of the firing trigger 90. As discussed hereinabove, the safety button 176 is retained in this position by the safety biasing member 182. To release the firing mechanism, the safety button 176 is depressed radially inwardly from the secured position of FIG. 37 to the unsecured position of FIG. 38 which causes the wedge segment 178 of the safety button 176 to disengage from the wedge receptacle 184 of the safety biasing member 182 enabling the firing lock segment 180 to disengage from the firing arm 94. In this position of the safety button 176, the firing arms 94 are capable of longitudinal or pivotal movement.

Figure 39:
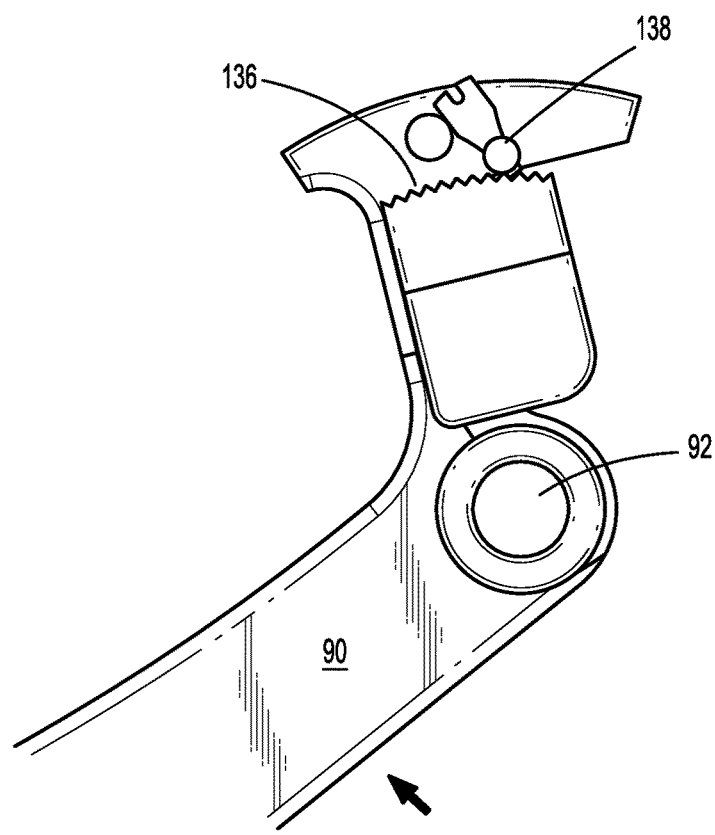
FIG. 39 is a view illustrating positioning of the pawl of the ratchet mechanism during movement of the firing trigger and activation of the firing mechanism.
Figure 40:
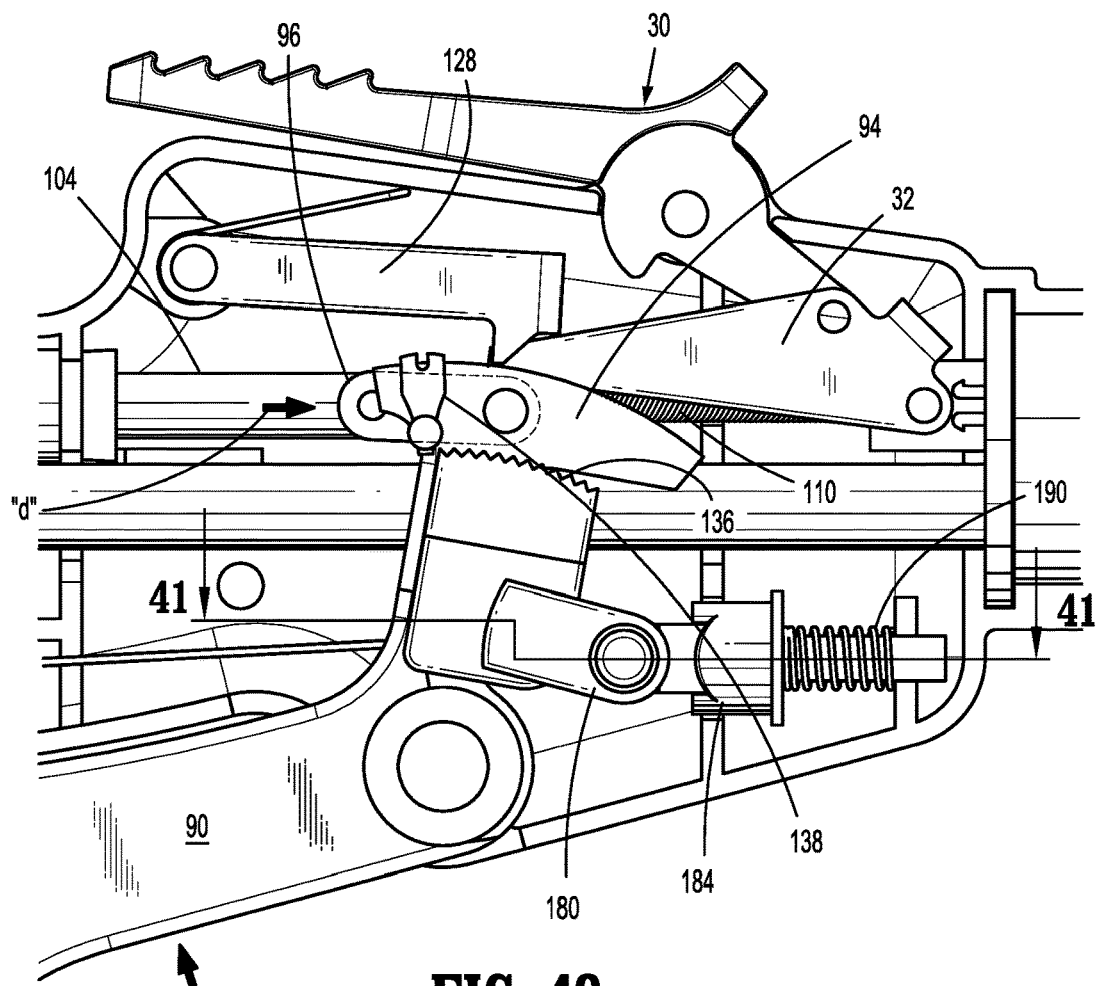
FIG. 40 is a side view of the handle with portions of the handle frame removed illustrating movement of the firing member during activation of the firing trigger.
Figure 41:
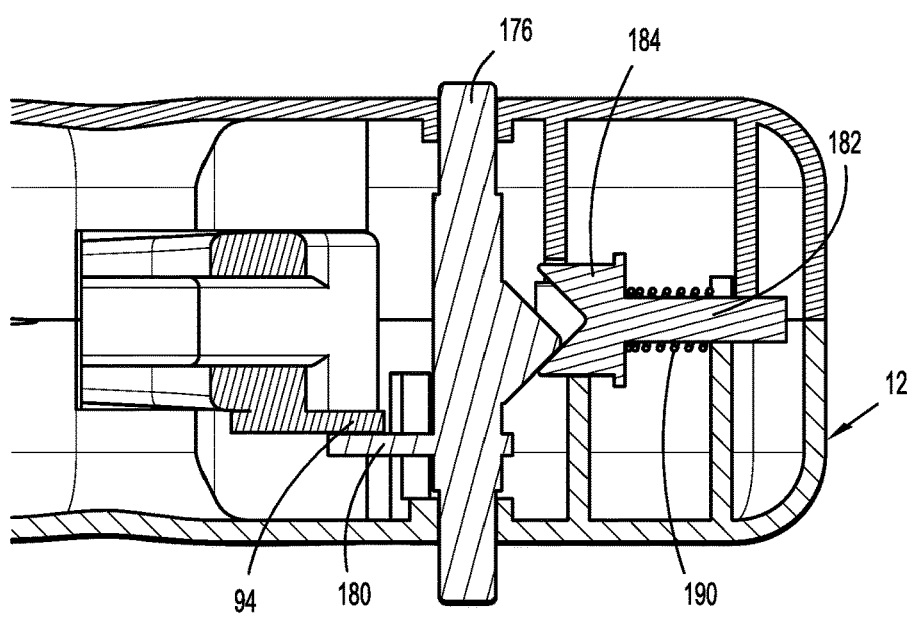
FIG. 41 is a cross-sectional view taken along the lines 41-41 of FIG. 40 illustrating the position of the safety button in the unsecured position during movement of the firing trigger.

Referring now to FIGS. 39-41, the firing stroke is initiated by pivoting the firing trigger 90 about pivot pin 92. FIG. 39 illustrates the pawl 138 of the ratchet mechanism engaging the ratchet teeth 136a of the ratchet 136 during the beginning of the firing stroke thus preventing return of the firing trigger 90 to the initial position. As the firing trigger 90 is pivoted toward the handle 12, the firing arms 94 and the firing links 96 drive the firing tube 104 in a distal direction. As depicted in FIG. 41, upon initiation of the firing stroke, the safety button 176 is prevented from returning to the secured position via engagement of the firing lock segment 180 of the safety button 176 with an outer surface of the firing arm 94.

Figure 43:
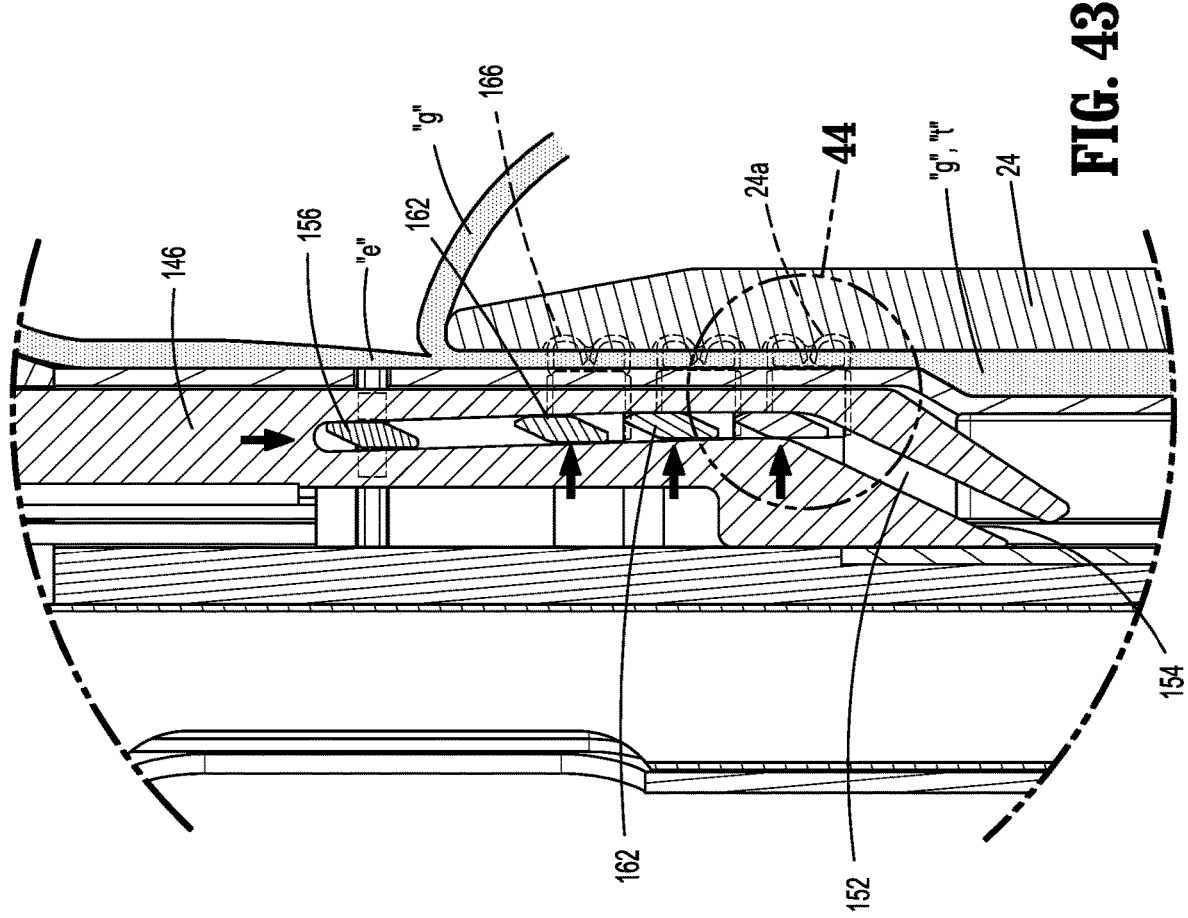
FIG. 43 is an enlarged isolated view of the area of detail identified in FIG. 42 illustrating deployment of the fasteners from the fastener cartridge.
Figure 42:
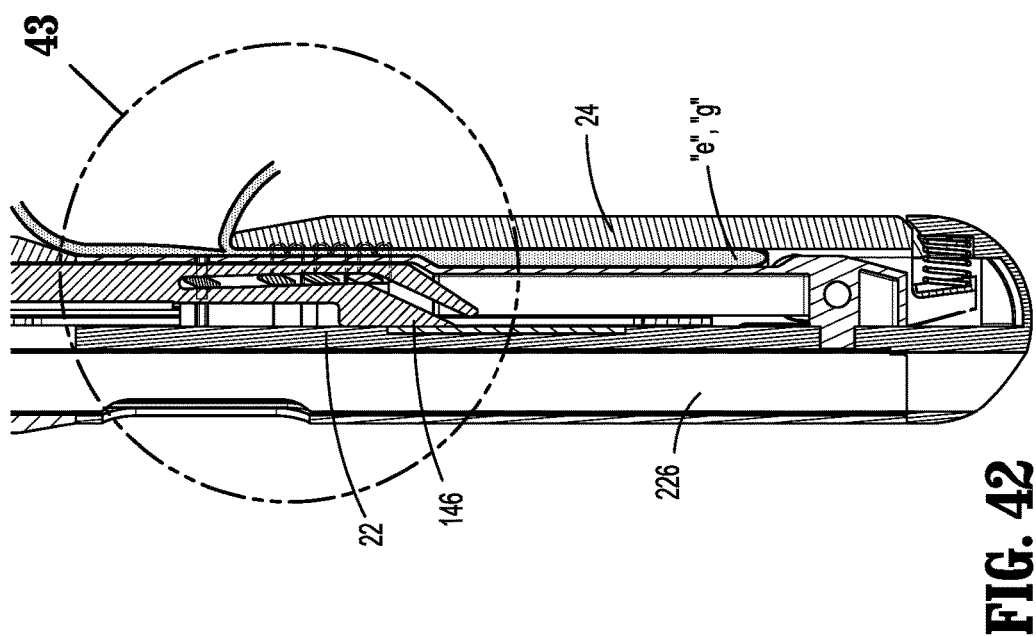
FIG. 42 is a side cross-sectional view illustrating the end effector in the approximated condition with the gastric and esophageal tissue clamped between the fastener cartridge and the anvil.
Figure 44:
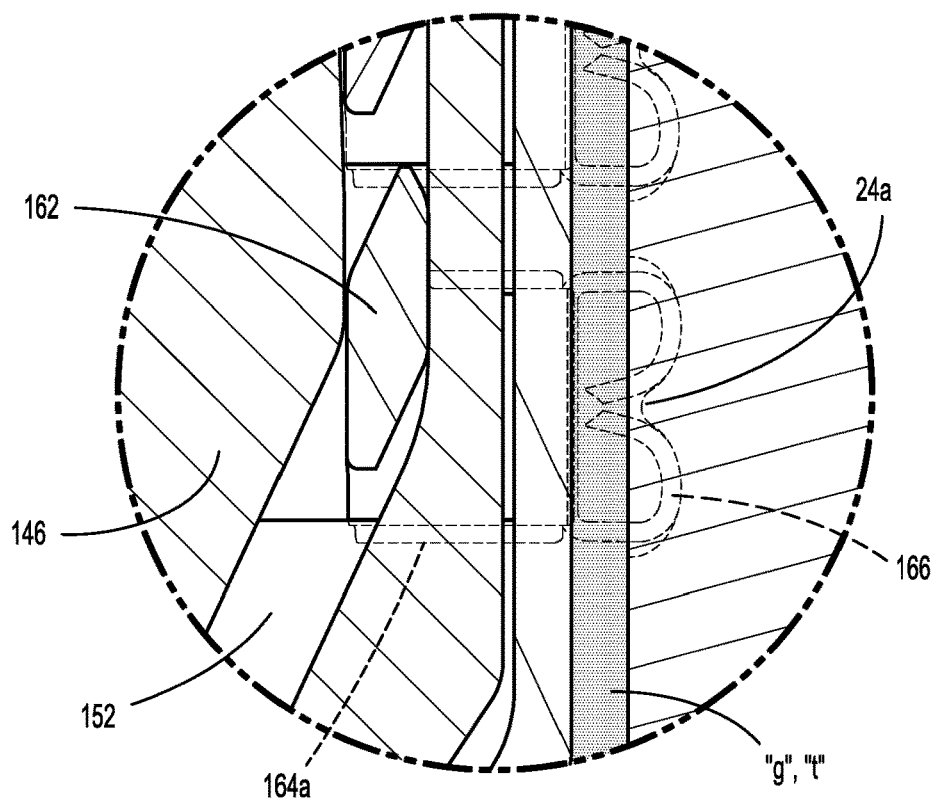
FIG. 44 is an enlarged isolated view of the area of detail identified in FIG. 43 illustrating formation of one fastener within a pocket in the anvil.

Referring now to FIGS. 42-44, during the firing stroke, the firing cam 146 distally advances such that the pusher cams 162 of the pushers 160 traverse the slot 152 within the firing cam 146. This motion drives the opposed pusher plates 164a, 164b (one shown in phantom in FIG. 44), attached to the pusher cams 162, into engagement with a first set of fasteners 166 within each row of fasteners for crimping or forming by the anvil 24, e.g., pockets 24a of the anvil 24. Upon completion of the firing stroke, two rows of fasteners 166 are fastened to the overlapped gastric "g" and esophageal tissue "et" with each row containing three fasteners 166. During the firing stroke, the separator 156 also traverses the slot 152 of the firing cam 146 to maintain appropriate spacing of the slot 152.

Figure 45:
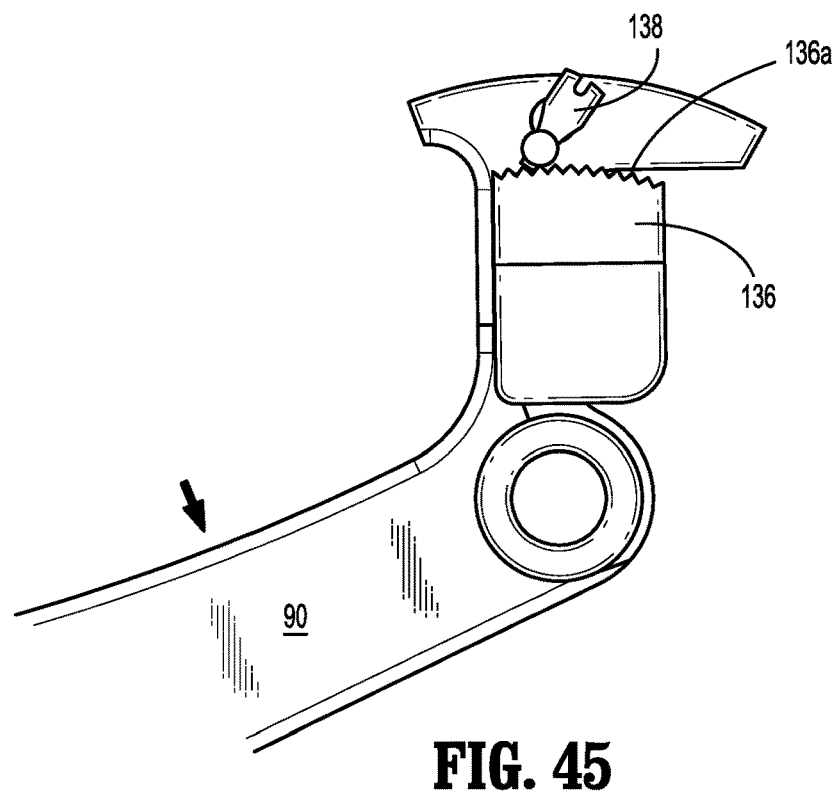
FIG. 45 is a view illustrating the pawl and ratchet mechanism during return of the firing trigger subsequent to actuation of the firing mechanism.
Figure 46:
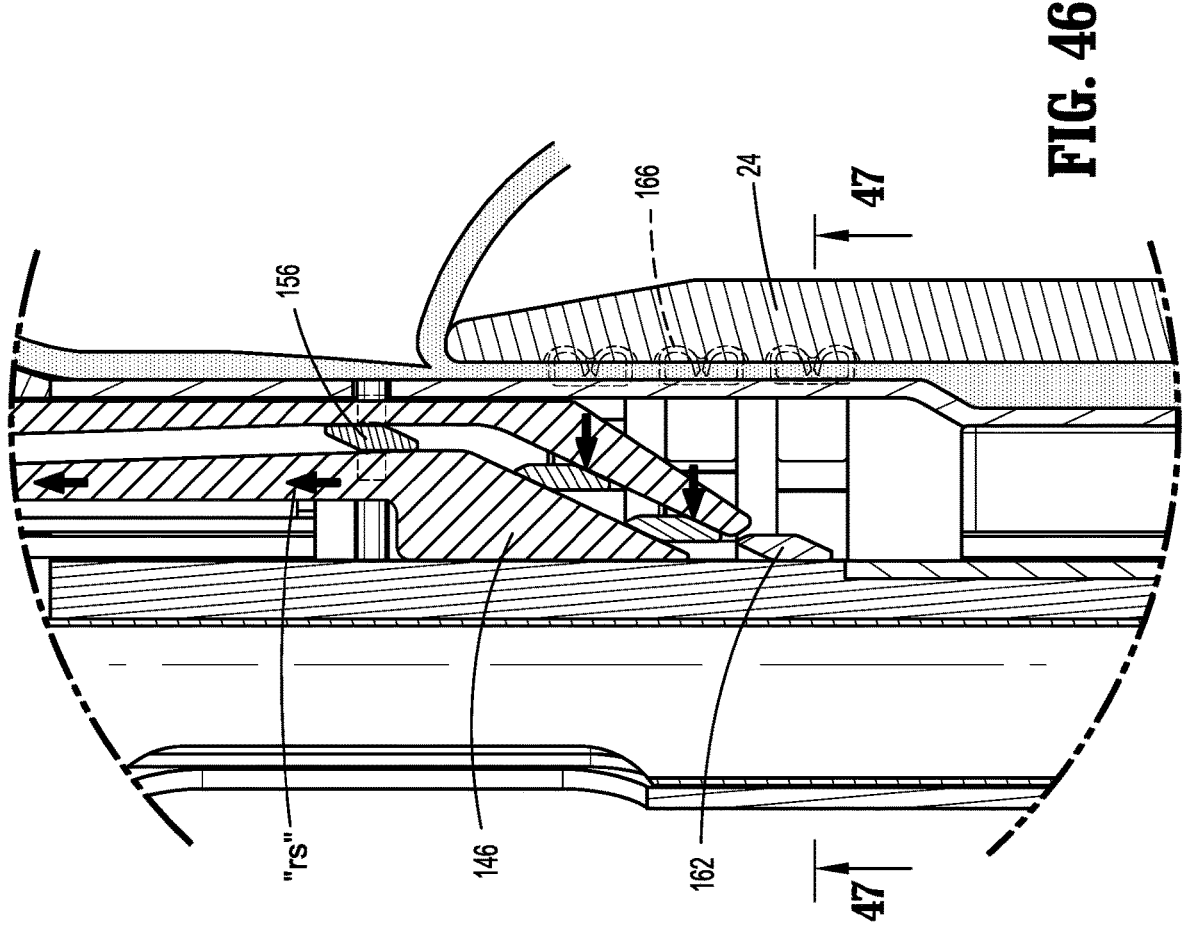
FIG. 46 is an enlarged cross-sectional view illustrating the pushers within the fastener cartridge being reset subsequent to actuation of the firing mechanism.
Figure 47:
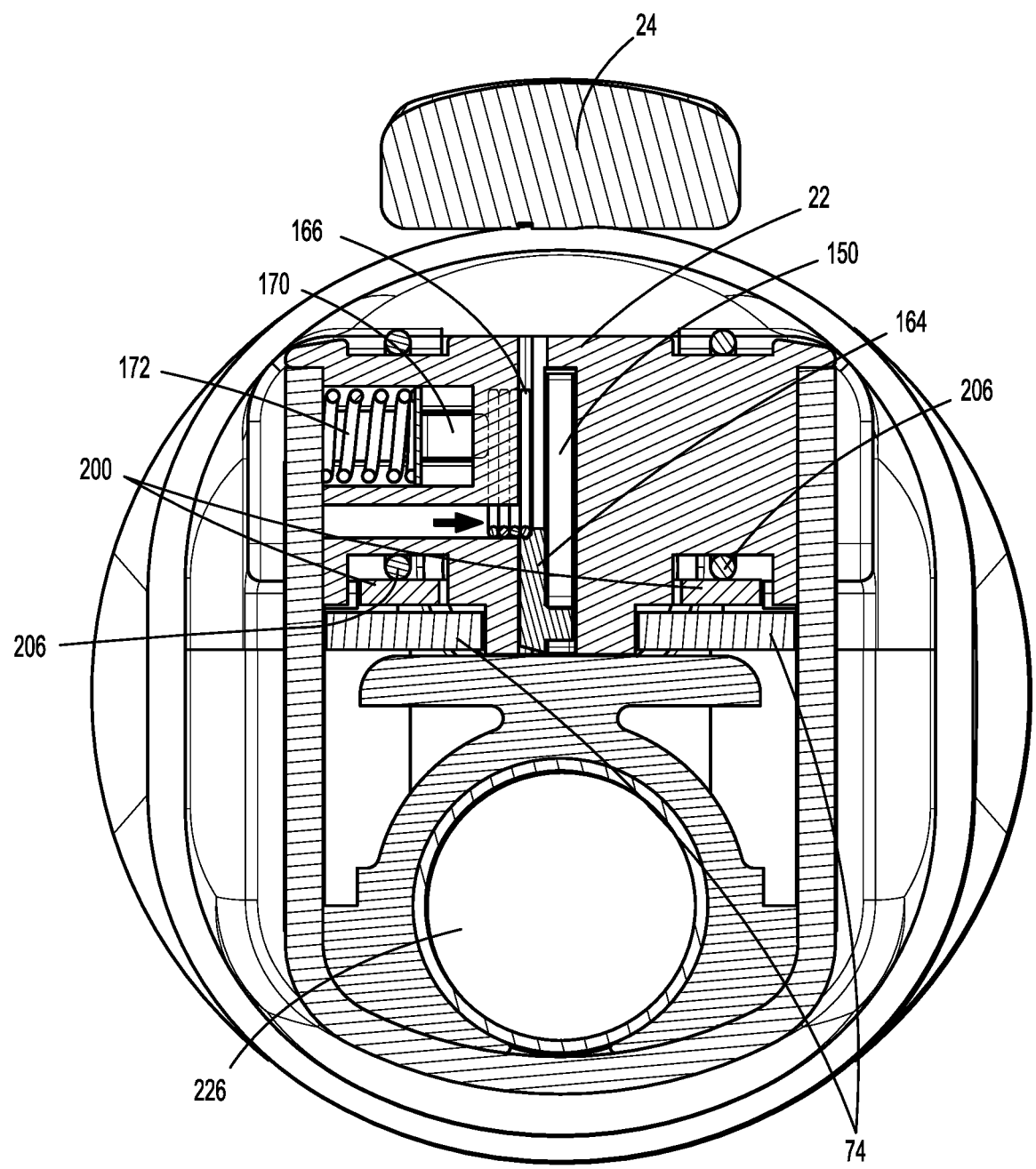
FIG. 47 is an axial cross-sectional view of the end effector along the lines 47-47 of FIG. 46 illustrating reloading of the fasteners within the fastener cartridge for a successive firing stroke.

Referring now to FIGS. 45-46, the firing trigger 90 is released to move to its initial position under the influence of spring 122 (FIG. 12) to cause the firing cam 146, firing tube 104 and the firing arms 94 to return in the direction of arrow "rs", e.g., a return stroke, to their initial positions. During this movement, the pawl 138 traverses the ratchet teeth 136a and the pushers 160 reset to their initial positions. The angular orientation of the ratchet teeth 136a and/or the pawl 138 permits return movement along the ratchet 136. As depicted in FIG. 47, upon complete return to the initial position of the firing trigger 90, the next set of fasteners 166 within each row is positioned into alignment with a respective pusher plate 164a, 164b under the influence of the pressure plates 170 and associated coil springs 172. The fastener apparatus 10 may then be maneuvered or rotated through a first sector of rotation to engage additional gastric and esophageal tissue "g", "et" to continue the fundoplication procedure. The fastener apparatus 10 is actuated to draw the gastric and esophageal tissue "g", "et" within the end effector 16 and the firing mechanism is activated to deliver another two rows of fasteners 166 within the tissue. The process is continued through rotation of the fastener apparatus 10 through a third sector of rotation followed by grasping of gastric and esophageal tissue "g", "et" and activation of the firing mechanism through another firing stroke. The process is repeated again to deliver a fourth set of fasteners. The entire fastening procedure is performed under visualization with the endoscope 300.

Figure 48:
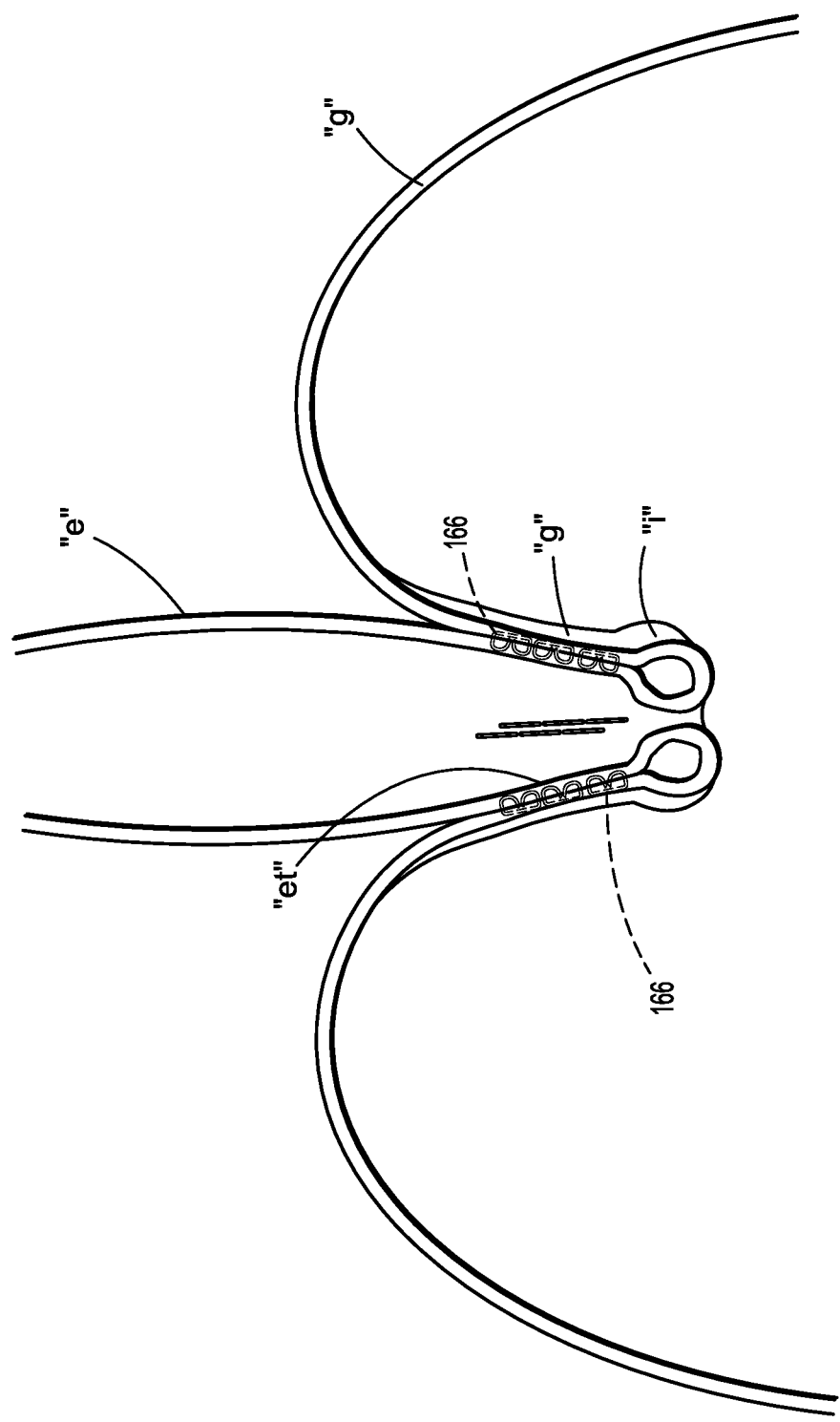
FIG. 48 is a view of the reflux valve "v" reconstructed through the use of the fastener apparatus.

FIG. 48 illustrates a reconstructed reflux valve "v" created through the use of the fastener apparatus 10. The provision of four rows of fasteners with multiple (e.g., three) fasteners in each row constructs a valve of adequate length and circumference thereby increasing the potential of success of the fundoplication. The fastener apparatus 10 creates or reconstructs the reflux valve "v" entirely through a transoral approach without requiring incisions or access through the abdominal cavity. The fastener apparatus 10 is able to perform the fundoplication procedure without removal of the fastener apparatus 10 and under complete visualization via the inserted endoscope 300. The associated mechanisms reduce or eliminate the potential of inadvertent activation of the firing mechanism until the end effector 16 is in the proper condition and the surgeon is prepared to initiate the firing procedure. The double pulley and grasper system ensures a substantial volume of gastric and esophageal tissue is engaged within the approximated end effector 16 thereby improving the success of the fastening procedure.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A surgical fastener apparatus, which comprises:
    a handle;
    a flexible elongate segment extending from the handle, the elongate segment having proximal and distal ends;
    an end effector defining a longitudinal axis mounted to the distal end of the elongate segment, the end effector including a fastener cartridge having an inner tissue engaging surface and an anvil, the fastener cartridge including a plurality of fasteners, the fastener cartridge and the anvil configured for relative movement between an open condition and an approximated condition of the end effector;
    an approximator member coupled to the end effector, the approximator member movable relative to the longitudinal axis to cause relative movement of the fastener cartridge and the anvil between the open condition and the approximated condition;
    a fastener drive operatively coupled to the fastener cartridge, the fastener drive movable to deploy the fasteners from the fastener cartridge for forming by the anvil;
    at least one tissue grasper secured to the fastener cartridge for longitudinal movement along the inner tissue engaging surface of the fastener cartridge along a fixed path between ends of the fastener cartridge, the at least one tissue grasper extending inwardly from the inner tissue engaging surface to engage tissue portions and draw the tissue portions between the fastener cartridge and the anvil when in the open condition; and
    at least one manual actuator mounted relative to the handle to actuate at least one of the approximator member, the fastener drive or the at least one tissue grasper.

2. The surgical fastener apparatus according to claim 1, wherein the at least one tissue grasper includes first and second tissue graspers, the first and second tissue graspers radially spaced relative to the longitudinal axis.

3. The surgical fastener apparatus according to claim 2 including a grasper actuator mounted relative to the handle and operatively coupled to the first and second tissue graspers, the grasper actuator movable to cause corresponding longitudinal movement of the first and second tissue graspers to draw the tissue portions between the fastener cartridge and the anvil.

4. The surgical fastener apparatus according to claim 3 including:
    a grasper drive operatively coupled to the grasper actuator and movable upon movement of the grasper actuator; and
    first and second pulley mechanisms coupled to respective first and second tissue graspers and to the grasper drive, and being actuable upon corresponding movement of the grasper actuator and the grasper drive.

5. The surgical fastener apparatus according to claim 4 wherein the first and second pulley mechanisms each includes a closed loop to which the respective first and second tissue graspers are secured, the closed loops movable to distally advance the first and second tissue graspers to draw the tissue portions between the fastener cartridge and the anvil.

6. The surgical fastener apparatus according to claim 1 including a manually operable firing trigger mounted relative to the handle and coupled to the fastener drive, the firing trigger movable to cause corresponding movement of the fastener drive to deploy the fasteners from the fastener cartridge.

7. The surgical fastener apparatus according to claim 6 including an approximator actuator mounted relative to the handle and operatively coupled to the approximator member, the approximator actuator movable relative to the handle between a first position and a second position to cause corresponding movement of the fastener cartridge and the anvil between the open condition and the approximated condition.

8. The surgical fastener apparatus according to claim 7 including a trigger lock couplable to the firing trigger, the trigger lock configured to prevent actuation of the firing trigger when the fastener cartridge and the anvil are in the open condition and permit actuation of the firing trigger when the fastener cartridge and the anvil are in the approximated condition.

9. The surgical fastener apparatus according to claim 8 wherein the trigger lock includes a lock member, the lock member movable between a lock position and a release position relative to the firing trigger.

10. The surgical fastener apparatus according to claim 9 wherein the approximator actuator is operatively couplable to the lock member whereby, upon movement of the approximator actuator to the second position, the lock member is moved to the release position.

11. The surgical fastener apparatus according to claim 10 wherein the lock member is normally biased to the lock position.

12. The surgical fastener apparatus according to claim 11 wherein the approximator actuator is normally biased to the first position.

13. The surgical fastener apparatus according to claim 6 including a manually operable safety button mounted to the handle and operably couplable with the firing trigger, the safety button movable between a secured position relative to the firing trigger to prevent movement of the firing trigger and an unsecured position to release the firing trigger.

14. The surgical fastener apparatus according to claim 13 including a safety biasing member mounted to the handle and engageable with the safety button, the safety biasing member selectively retaining the safety button in the secured position.

15. The surgical fastener apparatus according to claim 1 including a vacuum conduit extending along the elongate segment and having at least one fluid port adjacent the distal end of the elongate segment, the vacuum conduit couplable to a vacuum source to subject tissue surrounding the elongate segment to negative pressure.

16. The surgical fastener apparatus according to claim 15 wherein the elongate segment includes a vacuum distributor mounted adjacent the distal end of the elongate segment, the vacuum distributor including a plurality of vacuum grooves in fluid communication with the at least one fluid port for conveying the negative pressure.

17. The surgical fastener apparatus according to claim 16 wherein the elongate segment includes an outer sleeve, the outer sleeve coaxially mounted about the vacuum distributor and having a plurality of vacuum apertures in fluid communication with the vacuum grooves of the vacuum distributor for conveying the negative pressure.

18. The surgical fastener apparatus according to claim 1 wherein the handle and the elongate segment define an endoscope channel therethrough for reception of an endoscope.

19. The surgical fastener apparatus according to claim 18 wherein the elongate segment defines a lateral visualization window in visual communication with the endoscope channel to permit lateral viewing with the endoscope.

20. A surgical fastener apparatus comprising:
a handle;
a flexible elongate segment extending from the handle, the elongate segment having proximal and distal ends;
an end effector defining a longitudinal axis mounted to the distal end of the elongate segment, the end effector including a fastener cartridge and an anvil, the fastener cartridge having an inner tissue engaging surface including a plurality of fasteners, the fastener cartridge and the anvil configured for relative movement between an open condition and an approximated condition of the end effector;
an approximator member coupled to the end effector, the approximator member movable relative to the longitudinal axis to cause relative movement of the fastener cartridge and the anvil between the open condition and the approximated condition;
a fastener drive operatively coupled to the fastener cartridge, the fastener drive movable to deploy the fasteners from the fastener cartridge for forming by the anvil;
at least one tissue grasper secured to the fastener cartridge for longitudinal movement along the inner tissue engaging surface of the fastener cartridge along a fixed path between ends of the fastener cartridge, the at least one tissue grasper mounted for movement relative to the fastener cartridge and extending inwardly from the tissue engaging surface to engage tissue portions and draw the tissue portions between the fastener cartridge and the anvil when in the open condition, the at least one tissue grasper including first and second tissue graspers, the first and second tissue graspers radially spaced relative to the longitudinal axis; and
at least one manual actuator mounted relative to the handle to actuate at least one of the approximator member, the fastener drive or the at least one tissue grasper;
a grasper actuator mounted relative to the handle and operatively coupled to the first and second tissue graspers, the grasper actuator movable to cause corresponding longitudinal movement of the first and second tissue graspers to draw the tissue portions between the fastener cartridge and the anvil;
a grasper drive operatively coupled to the grasper actuator and movable upon movement of the grasper actuator;
first and second pulley mechanisms coupled to respective first and second tissue graspers and to the grasper drive, and being actuable upon corresponding movement of the grasper actuator and the grasper drive, the first and second pulley mechanisms each including a closed loop to which the respective first and second tissue graspers are secured, the closed loops movable to distally advance the first and second tissue graspers to draw the tissue portions between the fastener cartridge and the anvil,
a manually operable firing trigger mounted relative to the handle and coupled to the fastener drive, the firing trigger movable to cause corresponding movement of the fastener drive to deploy the fasteners from the fastener cartridge;
an approximator actuator mounted relative to the handle and operatively coupled to the approximator member, the approximator actuator movable relative to the handle between a first position and a second position to cause corresponding movement of the fastener cartridge and the anvil between the open condition and the approximated condition;
a trigger lock couplable to the firing trigger, the trigger lock configured to prevent actuation of the firing trigger when the fastener cartridge and the anvil are in the open condition and permit actuation of the firing trigger when the fastener cartridge and the anvil are in the approximated condition, the trigger lock including a lock member, the lock member movable between a lock position and a release position relative to the firing trigger, the approximator actuator being operatively couplable to the lock member whereby, upon movement of the approximator actuator to the second position, the lock member is moved to the release position, wherein the lock member is normally biased to the lock position and the approximator actuator is normally biased to the first position,
a vacuum conduit extending along the elongate segment and having at least one fluid port adjacent the distal end of the elongate segment, the vacuum conduit couplable to a vacuum source to subject tissue surrounding the elongate segment to negative pressure, the elongate segment including a vacuum distributor mounted adjacent the distal end of the elongate segment, the vacuum distributor including a plurality of vacuum grooves in fluid communication with the at least one fluid port for conveying the negative pressure, wherein the elongate segment includes an outer sleeve, the outer sleeve coaxially mounted about the vacuum distributor and having a plurality of vacuum apertures in fluid communication with the vacuum grooves of the vacuum distributor for conveying the negative pressure;
a manually operable safety button mounted to the handle and operably couplable with the firing trigger, the safety button movable between a secured position relative to the firing trigger to prevent movement of the firing trigger and an unsecured position to release the firing trigger; and
a safety biasing member mounted to the handle and engageable with the safety button, the safety biasing member selectively retaining the safety button in the secured position,
wherein the handle and the elongate segment define an endoscope channel therethrough for reception of an endo scope, the elongate segment defining a lateral visualization window in visual communication with the endoscope channel to permit lateral viewing with the endoscope.

\* \* \* \* \*